(12) United States Patent
Jain et al.

(10) Patent No.: US 11,369,789 B2
(45) Date of Patent: Jun. 28, 2022

(54) TRANSDERMAL DRUG DELIVERY SYSTEM

(71) Applicants: Ishaan Jain, Potomac, MD (US); Anjan S. Sesetty, Clarksburg, MD (US); Aditi Gubba, Boyds, MD (US); Om G. Desai, Boyds, MD (US)

(72) Inventors: Ishaan Jain, Potomac, MD (US); Anjan S. Sesetty, Clarksburg, MD (US); Aditi Gubba, Boyds, MD (US); Om G. Desai, Boyds, MD (US)

(*) Notice: Subject to any disclaimer, the term of this patent is extended or adjusted under 35 U.S.C. 154(b) by 0 days.

(21) Appl. No.: 17/222,226

(22) Filed: Apr. 5, 2021

(65) Prior Publication Data
US 2021/0228869 A1  Jul. 29, 2021

(51) Int. Cl.
*A61N 1/30* (2006.01)
*A61N 1/36* (2006.01)
*A61N 1/04* (2006.01)

(52) U.S. Cl.
CPC ........... *A61N 1/303* (2013.01); *A61N 1/0448* (2013.01); *A61N 1/36021* (2013.01); *A61N 1/36031* (2017.08)

(58) Field of Classification Search
CPC .............. A61N 1/36021; A61N 1/0448; A61N 1/36031; A61N 1/303
See application file for complete search history.

(56) References Cited

U.S. PATENT DOCUMENTS

| | | |
|---|---|---|
| 6,424,862 B1 | 7/2002 | Brown, III et al. |
| 6,745,071 B1 | 6/2004 | Anderson et al. |
| 7,004,929 B2 | 2/2006 | Mcwethy et al. |
| 7,344,894 B2 | 3/2008 | Greenstein et al. |
| 7,717,877 B2 | 5/2010 | Lavi et al. |
| 8,357,114 B2 | 1/2013 | Poutiatine et al. |
| 8,480,632 B2 | 7/2013 | Miller et al. |
| 8,696,637 B2 | 4/2014 | Ross |
| 8,911,773 B2 | 12/2014 | Kimball |
| 9,314,527 B2 | 4/2016 | Cottrell et al. |

(Continued)

FOREIGN PATENT DOCUMENTS

EP  2612645 B1  3/2020

OTHER PUBLICATIONS

McConville, A., et al., "A wireless smart patch for the controlled repetitive transdermal administration of therapeutic agents," Sensors and Actuators B: Chemical, vol. 294, 2019, pp. 24-31.

(Continued)

*Primary Examiner* — Joseph M Dietrich
(74) *Attorney, Agent, or Firm* — Dave Law Group LLC; Raj S. Dave

(57) ABSTRACT

An embodiment relates to a transdermal drug delivery system comprising a patch comprising a) a cartridge comprising a drug; b) a bio-sensor and a non bio-sensor; c) an active delivery pad comprising an electrode for delivery of the drug into a tissue via iontophoresis; d) a power source of electrical energy connected to the electrode; e) a microcontroller configured to control a release of the drug wherein the patch is attached to the tissue via an adhesive pad, and optionally top of patch is covered with a sheet; wherein the bio-sensor is configured to detect a physiological parameter; wherein the non bio-sensor is configured with a software to control working of the patch.

20 Claims, 9 Drawing Sheets

Doctor is able to refill cartridge by entering a password on the app to open compartment Drug Flow from cartridge to active pad reservoir Funnel door opens and closes based on scheduled drug releases

(56) References Cited

U.S. PATENT DOCUMENTS

| | | |
|---|---|---|
| 9,944,835 B2 | 4/2018 | Sherman et al. |
| 10,603,440 B2 | 3/2020 | McCaffrey et al. |
| 10,610,128 B2 | 4/2020 | Zdeblick et al. |
| 10,647,032 B2 | 5/2020 | Radcliffe et al. |
| 10,745,601 B2 | 8/2020 | Parker et al. |
| 10,806,924 B2 | 10/2020 | Imran et al. |
| 2007/0083186 A1 | 4/2007 | Carter et al. |
| 2008/0004564 A1 | 1/2008 | Smith |
| 2011/0144586 A1 | 6/2011 | Michaud et al. |
| 2013/0197430 A1* | 8/2013 | Olson .................. A61B 5/0836 604/66 |
| 2015/0045722 A1* | 2/2015 | Imran ...................... A61N 1/30 604/20 |
| 2015/0273148 A1* | 10/2015 | Sexton .................. A61M 5/158 604/891.1 |
| 2016/0235975 A1 | 8/2016 | Jung |
| 2018/0214631 A1 | 8/2018 | Amirouche |
| 2019/0216321 A1* | 7/2019 | Grande .................. A61B 5/024 |
| 2019/0231707 A1 | 8/2019 | Stiles et al. |
| 2020/0289488 A1 | 9/2020 | Venkatraman et al. |

OTHER PUBLICATIONS

Yang, J., et al., "Smartphone-powered iontophoresis-microneedle array patch for controlled transdermal delivery," Microsystems & Nanoengineering 6, Article No. 112, 2020, pp. 1-14.

\* cited by examiner

TRANSDERMAL DRUG DELIVERY SYSTEM

FIELD OF THE INVENTION

The present invention relates to transdermal delivery of a therapeutic drug by iontophoresis and systems comprising thereof. More specifically, this invention relates to the automatic transdermal delivery of opioid and opioid antagonist.

BACKGROUND OF INVENTION

Hospital patients and out-patients experience negative effects from various pharmaceutical drugs prescribed for treatment. These negative effects may be due to overdose, under dose or adverse reactions to these drugs. For an example, opioids are often given to patients for pain management as its use is considered safe for most patients. However, opioids may lead to adverse reactions because of excessive dosing, improper monitoring, medication interactions and undesired reactions with other drugs. Adverse effects due to opioids vary from respiratory depression, sedation, dizziness, nausea, vomiting, constipation, physical dependence etc.

Opioid crisis has been ongoing since the 1990s. Even with introduction of faster equipment, more complex technologies, and efficient distribution services, this issue isn't going anywhere. Around 48,000 deaths per year is attributed to opioid overdoses. As per survey, in 2008, there were four times as many deaths due to overdose than there were in 1999. According to the Centers for Disease Control and Prevention (CDC), the death rate from overdoses of opioid tripled from 6.1 per 100,000 people in 1999 to 19.8 in 2016 and rose 20% from 2015 to 2016. According to a report on the leading cause of deaths from injury in the United States, half of deaths due to drug overdose are related to prescription drugs.

In 2017, the U.S. Department of Health and Human Services (HHS) announced a public health emergency due to an increase in the misuse of opioids. The administration introduced a strategic framework called the Five-Point Opioid Strategy, which includes providing access recovery services, increasing the availability of reversing agents for overdose, funding opioid misuse and pain research, changing treatments of people managing pain, and updating public health reports related to combating opioid drug misuse.

Iontophoresis is a method of administering a compound to a subject by applying an electric current to the skin of the subject so as to transdermal deliver the drug to the subject through its skin.

U.S. Pat. No. 6,171,294 discloses, "an improved electrotransport drug delivery system for analgesic drugs, namely fentanyl and sufentanil." Similarly, US 6,216,03 also discloses, "an improved electrotransport drug delivery system for analgesic drugs, namely fentanyl and sufentanil."

However, the currently available iontophoretic drug delivery systems does not provide a mechanism for a controlled and proper reversing agent during opioid overdose. There is need of drug delivery device which provides for improved safety and ease of use to combat opioid overdose.

SUMMARY OF INVENTION

The present invention provides a convenient, comfortable, and safe solution for any person who requires a drug prescription. The system advantageously utilizes physiological conditions of user so as to automatically give at least one drug or medicine when certain criteria are met. The system has a multitude of safeguards to prevent possible misuse of the medication within the patch. It is the first drug delivery system which is fully autonomous and can be controlled from a remote app on a mobile device or laptop. Whether the patient has a history with drug-abuse or not, this medical patch encompasses various safeguards and design-features, which makes it the most convenient and user-friendly drug delivery system.

An embodiment relates to a transdermal drug delivery system comprising a patch comprising: a) a cartridge comprising a drug; b) a bio-sensor and a non bio-sensor; c) an active delivery pad comprising an electrode for delivery of the drug into a tissue via iontophoresis; d) a power source of electrical energy connected to the electrode; e) a microcontroller configured to control a release of the drug wherein the patch is attached to the tissue via an adhesive pad, and optionally top of patch is covered with a sheet; wherein the bio-sensor is configured to detect a physiological parameter; wherein the non bio-sensor is configured with a software to control working of the patch.

In an embodiment, the non-biosensor is configured with a software to control working of the patch; wherein the biosensor comprises a blood pressure sensor, a temperature sensor, and a heart rate sensor, a tactile sensor; and wherein the non-bio-sensor comprises a BLE sensor.

In an embodiment, the patch comprises a first cartridge comprising a first drug and a second cartridge comprising a second drug wherein the first cartridge and second cartridge are separated from each other.

In an embodiment, the electrode comprises of zinc and silver chloride electrode, and wherein the drug comprises an opioid drug, non-opioid drug, an opioid antagonist comprising Naloxone.

In an embodiment, the adhesive pad comprises a substrate comprising an activated charcoal, and an adhesive material comprising a Polycarbonate adhesive, and wherein the sheet comprises lignin.

In an embodiment, the release of the drug starts on a signal, wherein the signal is regulated manually comprising a release button or automatically based on physiological condition of a user.

In an embodiment, the software sends an alert to an user on a working condition of the patch, wherein the working condition includes an overdose of the drug, an accidental loss of the patch, a defunct power source, an empty cartridge or any combination thereof.

In an embodiment, the patch further comprises a first system to replace the power source and/or to recharge the power source, and a second system to refill the cartridge.

In an embodiment, the patch has any shape or any size.

In an embodiment, a system comprising a patch comprising: a tissue contacting side comprising an adhesive layer and an active delivery pad; a non-tissue contacting side comprising: a biosensor to configure a medical characteristic of a user, at least a first electrode and a second electrode wherein each of the first electrode and the second electrode is coupled respectively to a first reservoir containing a first drug and a second reservoir containing a second drug, a source of electric power connected in a circuit; and a microcontroller configured for controlling current flow in said circuit according to a signal from the biosensor to enable the plurality of successive doses of said drugs from said reservoirs, wherein the active delivery pad at the tissue contacting side allow for an iontophoretic transdermal delivery of the drug to the user through the tissue contacting side.

In an embodiment, electrodes comprise zinc or silver chloride electrode.

In an embodiment, reservoir comprises of cartridge and is configured to hold a plurality of drug forms, wherein cartridge is reusable. the first and second reservoirs are separated from one another, wherein first reservoir includes opioid and wherein the second reservoir includes opioid antagonist comprising Naloxone.

In an embodiment, the source of electric power comprises a battery, wherein the battery comprises a coin battery, or a rechargeable mini battery. In an embodiment, a method to regulate release of a drug comprising: attaching a patch, sending a signal to start an electric current flow, transferring of the drug by an iontophoretic transdermal delivery system, wherein release of the drug is controlled by the microcontroller.

In an embodiment, a method to regulate release of a drug comprising: attaching a patch, sending a signal to start an electric current flow, transferring of the drug by an iontophoretic transdermal delivery system, wherein release of the drug is controlled by the microcontroller; wherein release rate of the drug is $R_d = (t_d \, IM_d)/(z_d \, F)$ Wherein Rd=rate of transdermal delivery of the drug, td is the transport number or a fraction of charge that is carried by an ion of the drug, I is the current, Md is molecular weight of the ion of the drug, zd is the valence of the ion of the drug, F is Faraday's Constant.

In one embodiment, a system comprising a patch comprising: a substrate having a tissue contacting side and a non-tissue contacting side, electrodes comprising a first electrode and a second electrode, a first reservoir comprising a first drug and a second reservoir comprising a second drug, a source of electric power connected in a circuit between the first reservoir and the second reservoir, a microcontroller configured for controlling a current flow in the circuit to enable a plurality of successive doses of the first drug and/or the second drug from the first reservoir and/or the second reservoir; wherein each of the first electrode and the second electrode are coupled to the first reservoir and the second reservoir respectively, wherein the tissue contacting side comprises an adhesive layer that allows transdermal delivery to a patient of the first drug and the second drug, and wherein the system is configured to be an automatic and self-controlled transdermal drug delivery system.

In an embodiment, the electrodes comprise wires that are round, circular and/or coated wires.

In an embodiment, wires are coated with zinc chloride or silver chloride, and wherein an anode comprises the zinc chloride and a cathode comprises the silver chloride.

In an embodiment the first reservoir and/or the second reservoir comprises a cartridge that is configured to hold a plurality of drug forms.

In an embodiment, the cartridge is partially reusable or fully reusable.

In an embodiment, the first reservoir and the second reservoir are separated from one another.

In an embodiment, the first reservoir comprises an opioid, an opioid agonist or a partial opioid agonist.

In an embodiment, the second reservoir comprises an opioid antagonist.

In an embodiment, the opioid antagonist includes naloxone.

In an embodiment, wherein the source of electric power comprises a battery.

In an embodiment, the system further comprising a biosensor coupled to the microcontroller to verify a medical characteristic of the patient prior to delivery of the opioid, the opioid agonist or the partial opioid agonist.

In an embodiment, the microcontroller is configured to analyze the medical characteristic of the patient to determine a symptom associated with an opioid overdose in the patient.

In an embodiment, the microcontroller is configured to analyze the medical characteristic of the patient to determine a symptom associated with an opioid overdose in the patient; wherein the symptom corresponds to a decrease in respiratory rate, a decrease in heart rate, a decrease in blood pressure, deviations from normal body temperature, passing out or an unresponsive loss of consciousness, skin color changes, abnormal breathing, fast, slow or irregular breathing, severe chest pain, seizures, severe headaches, difficulty in breathing, delirium, agitation, and/or anxiety.

In an embodiment, the microcontroller is further configured to send an alert or notification wirelessly upon detection of the symptom.

In an embodiment, the system further comprising a biosensor coupled to the microcontroller to verify a medical characteristic of the patient prior to delivery of the opioid, the opioid agonist or the partial opioid agonist; wherein the biosensor comprises a pulse oximeter, a heart rate sensor, an ECG sensor, a skin sensor, a temperature sensor, and/or a blood flow sensor.

In an embodiment, the source of electric power comprises a battery; the system further comprising a cover sheet covering the patch.

In an embodiment, the patch comprises any shape and any size.

In an embodiment, the shape comprises a rounded rectangle.

BRIEF DESCRIPTION OF THE FIGURES

The figures are furnished with the application to understand the invention sought to be patented. It shall not be construed as only way to perform the invention has sought to be patented.

DETAILED DESCRIPTION

Definitions and General Techniques

Figure 1:
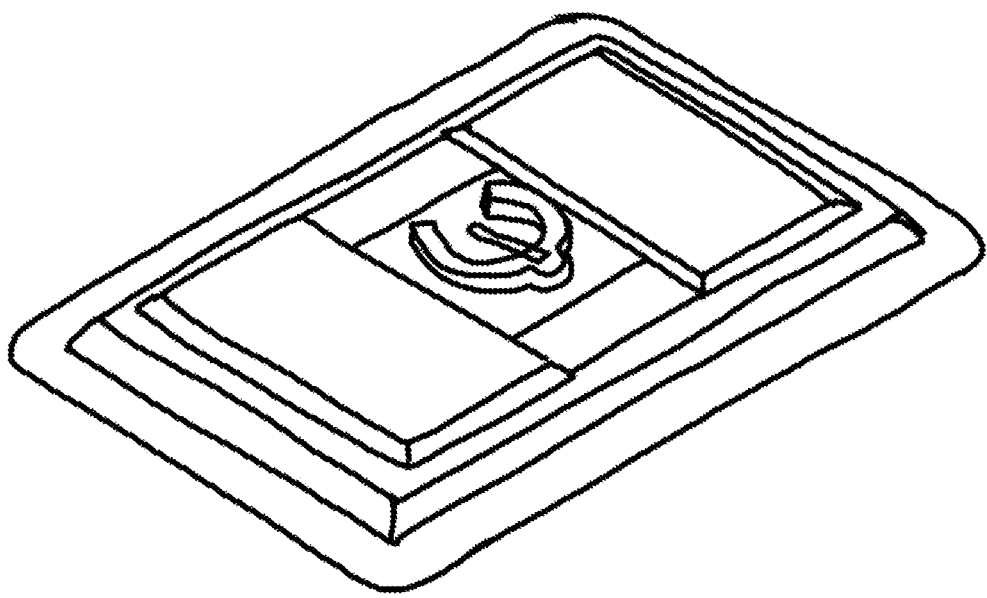
FIG. 1 illustrates a schematic representation of a patch system.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denotes the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment.

Furthermore, the features, structures, or characteristics may be combined in any suitable manner in one or more embodiments. Thus, the features, structures, or characteristics illustrated or described in connection with one embodiment may be combined, in whole or in part, with the features structures, or characteristics of one or more other embodiments without limitation. Such modifications and variations are intended to be included within the scope of the present invention.

The following terms and phrases, unless otherwise indicated, shall be understood to have the following meanings.

The term "transdermal" is a route of administration wherein ingredients are delivered across the skin for systemic distribution. Examples include transdermal patches used for medicine delivery. The drug is administered in the form of a patch or ointment that delivers the drug into the circulation for systemic effect. Transdermal administration can be accomplished by applying, pasting, rolling, attaching, pouring, pressing, rubbing, etc., of a transdermal preparation onto a skin surface.

The term "transdermal patch" refers to a matrix or liquid reservoir type of delivery device which is used to transdermally deliver doses of a substance, over a specific application period.

In an embodiment, the transdermal patch can be a peelable pouch, including a substantially flat enclosure formed by a first and a second opposing flexible plies. A seal can extend along at least a portion of a perimeter of the opposing plies. A flat, flexible transdermal patch can be disposed in the enclosure, the patch including a bioactive agent dissolved in a layer of adhesive. A release liner can be removably attached over the layer of adhesive. The patch and the release liner can together be sufficiently resilient so as to generate a spring force when displaced out of the flat configuration. The first and the second plies can each be separable along the seal and can be displaceable out of the flat configuration. The spring force generated by the patch and the release liner can be sufficient to overcome an adhesive force created by the adhesive between the patch and one of the plies.

In an embodiment, a transdermal patch is typically a small adhesive bandage that contains the drug to be delivered and these bandages can take several forms. The simplest type is an adhesive monolith comprising a drug-containing reservoir disposed on a backing. The reservoir is typically formed from a pharmaceutically acceptable pressure sensitive adhesive but, in some cases, can be formed from a non-adhesive material, the skin-contacting surface of which is provided with a thin layer of a suitable adhesive. The rate at which the drug is administered to the patient from these patches can vary due to normal person-to-person and skin site-to-skin site variations in the permeability of skin to the drug.

In an embodiment, the transdermal patch can easily deliver a controlled volume of a fluidic drug compound to skin is provided. More particularly, the patch contains a microneedle assembly that is configured to be placed in fluid communication with a drug delivery assembly. The microneedle assembly contains a support and a plurality of microneedles that extend outwardly from the support. The microneedles are formed with one or more channels of a certain dimension such that passive capillary flow drives a flow of the drug compound. The drug delivery assembly contains a reservoir for the drug compound that is in fluid communication with a rate control membrane that helps control a flow rate of the drug compound by modulating a pressure of the drug compound, downstream from the reservoir. A release member is also positioned adjacent to the microneedle and drug delivery assemblies. Prior to use, the release member acts as a barrier to the flow of the drug compound and thus inhibits premature leakage. In this manner, the patch can initially be provided in an "inactive" configuration in which the drug compound is securely retained. When it is desired to release the drug compound, the patch can simply be activated by at least partially separating the release member from the drug delivery and microneedle assemblies.

In an embodiment, patches are multi-layer laminate or liquid reservoir type patches in which a drug release rate controlling membrane is disposed between the drug reservoir and the skin contact adhesive. This membrane serves to reduce the effect of fluctuations in skin permeability by reducing the in vitro release rate of the drug from the patch. This type of patch is generally preferred when a significantly more potent drug is administered, but to achieve a similar rate of drug delivery, it usually has to cover a larger area of skin than a monolithic patch.

In an embodiment, a transdermal patch for administration of a biologically active compound comprising the composition or matrix layer. The composition or matrix layer can be a solid or semi-solid layer. A matrix layer suitable for administering a transdermal patch of a biologically active compound can comprising a combination of mono-(tocopherol) phosphate and di-(tocopherol) phosphate, and selected from the group consisting of acrylates and papyride a polymer of a group consisting of povidones, decane, polyvinylpyrrolidone, polyoxyalkylene, amine-resistant polyoxyalkylene, polyalkyl acrylate, and polymethyl methacrylate Agent. The composition or matrix layer can also contain a polymeric carrier.

In an embodiment, transdermal patch or any component of the patch such as release layer, peelable, matrix layer, polymeric carrier, or any additional layer in the patch etc. can comprise natural and synthetic polymers, copolymers or terpolymers.

In an embodiment, natural polymers include rubber, elastomers, polysaccharides (such as cellulose), natural resins (such as shellac and amber). Synthetic polymers include, for example, acrylates, polyacrylates, polyalkyl acrylates, polyamines, polyesters, polycarbonates, polyimines, polystyrenes, acrylonitrile butadiene styrene, polyacrylonitrile, Polybutadiene, poly(butylene terephthalate), poly(ether oxime), poly(ether) ketone, polyethylene, poly(ethylene glycol), poly(ethylene terephthalate), poly Propylene, polytetrafluoroethylene, styrene-acrylonitrile resin, poly(trimethyl terephthalate), polyurethane, polyvinyl butyral, polyvinyl chloride, polydifluoroethylene, paclitaxone (povidone), poly(vinylpyrrolidone), polychloroprene, fluoroelastomer, chlorosulfonated rubber, hypromellose, polyolefin elastomer, polypropylene decylamine, Chlorinated polyethylene, polyether oxime, nylon (nylon), liquid crystal polymer, polyethylene terephthalate (PET), polyphenyl fluorene, polyamidovinyl alcohol derivative, polyethylene glycol, ethylene vinyl acetate, polymethyl methacrylate, cellulose derivatives (such as ethyl cellulose, hydroxypropyl methyl cellulose), sugar derivatives (gum) Derivatives of sorbitol and mannitol), poly silicon oil and polyethylene oxide derivatives, silicone oil, poly-silicon siloxane (which includes an amine-resistant silicone poly siloxane), and silicon oxide.

In an embodiment, transdermal Patch can also comprise of an additional layer. Additional layer may comprise of same of different material as of matrix layer.

The term "cartridge" is defined as a case or container that holds a substance, device, or material which may be difficult, troublesome, or awkward to handle and usually can be easily changed. For example: an ink cartridge. An ink cartridge or inkjet cartridge is a component of an inkjet printer that contains the ink that is deposited onto paper during printing. Each ink cartridge contains one or more ink reservoirs; certain producers also add electronic contacts and a chip that communicates with the printer.

In an embodiment, the cartridge may be coated or wrapped in a biodegradable film such as a polydioxanon film sold under the trademark PDS or with a Polyglyccrol sebacatc (PGS) film or other biodegradable films formed from PGA (Polyglycolic acid, marketed under the trade mark Vicryl), PCL.

In an embodiment, cartridge may be made up of natural and synthetic polymers, copolymers or terpolymers.

In an embodiment, the system may have a drilling mechanism to create an orifice in the cartridge to inject material into the cartridge. An evacuation mechanism to extract excess material from a used cartridge. This process could help in cleaning the used cartridges.

In an embodiment, the cartridge holding material such as a drug is positioned within the housing and the shield and includes a barrel, a stopper, and a needle extending toward the distal end of the housing. The barrel is arranged to contain a fluid in communication with the needle. The stopper is slidingly located within the barrel for forcing the fluid through the needle upon activation of the injector. The driver is in communication with the housing and the shield. The driver is arranged to act on the stopper when disengaged from the housing.

In an embodiment, the cartridge is located in a hollow barrel and is connected to the cartridge by a double-ended needle. The needle may be moved between a projecting position, where it is exposed for use, and a retracted position, where it is protected from accidental touch. A plunger is located at the rear of the barrel and engages the cartridge's rear end. By pressing down on the plunger, medication is ejected from the cartridge.

In an embodiment, a cartridge may include a fluid reservoir configured to be filled with a volume of the therapeutic fluid sufficient for a prolonged single infusion protocol. The cartridge may additionally include a delivery mechanism having a distal end in fluid communication with an interior volume of the fluid reservoir and a proximal end configured to couple to either the first drive mechanism or the second drive mechanism and be translated between a plurality of linear positions to deliver the therapeutic fluid to the patient. In addition, the infusion cartridge may be configured to be interchangeably coupled to, and alternated between, the first pump system and the second pump system during the single infusion protocol of the therapeutic fluid to the patient.

In an embodiment, a cartridge has a stopper is positioned in a first portion of the cartridge. A needle guide component is positioned within the cartridge stopper. A needle is positioned within a central opening of the needle guide. A plunger is positioned in a second portion of the cartridge. The plunger includes a fluid path pocket facing and aligned with the central opening of the needle guide component. The plunger is driven toward the cartridge stopper to expel the liquid drug from the cartridge through the needle. An end of the needle can be positioned within the fluid path pocket when the plunger is pushed against the cartridge stopper, ensuring that only a small volume of the liquid drug remains in the cartridge when delivery of the liquid drug is completed.

In an embodiment, a cartridge may comprise one or more compressible reservoirs that may contain the medicament, wherein the release of medicament from a compressible reservoir may be controlled by a pumping mechanism within the cartridge. In some aspects, a cartridge may be operable when paired or connected with a portable dispensing unit (sometimes referred to as a "PDU") or other device or system comprising a power source and control mechanism, such as a graphical user interface (sometimes referred to as a "GUI"), wherein the pumping mechanism may individually actuate a compressible reservoir and deliver medicaments continuously or at a programmable intermittent rate.

In an embodiment, a cartridge comprising one or more portions constructed of a material, wherein the one or more portions define an array of temperature-controlled zones including reactants, wherein each said temperature-controlled zones is constrained by cartridge portions that surround an area of space in which a reactant is contained and confine the reactant from flowing into other of said temperature-controlled zones, and wherein the cartridge portions include clear or translucent portions that allow direct irradiation of reactant molecules to facilitate thermal regulation of the reactants and to transmit light through the reactants.

The term "Drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation may include more than one therapeutic agent, wherein exemplary combinations of therapeutic agents include a combination of two or more drugs.

By way of example, and not limitation, drug substances suitable for use in the present invention include physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, and various mixtures, salts, prodrugs and co-drugs thereof.

Physiologically active peptides and/or proteins range in molecular weight front 200 to 100,000 and include but are not limited to human growth hormone, growth hormone releasing hormone, growth hormone releasing peptide, interferons, colony stimulating factors, interleukins, macrophage activating factors, macrophage peptide, B-cell factors, T-cell factors, protein A, allergy repressors, immunotoxins, lymphotoxins, tumor necrosis factors, tumor repression factors, vascular endothelial growth factor (VEGF), fibroblast growth factor (FGF), metastasis growth factors, alpha-1 antitrypsin, apolipoprotein-E, erythropoietin, Factor VII, Factor VIII, Factor IX, plasminogen activating factors, urokinase, streptokinase, Protein C, C-reactive protein, superoxide dismutase, platelet-derived growth factors, epidermal growth factors, osteogenic growth factors, osteogenesis-promoting proteins, calcitonin, insulin, atriopeptin, cartilage induction factors, connective tissue activating factors, follicle stimulating hormone, leutenizing hormone, leutenizing hormone releasing hormone, nerve growth factors, parathyroid hormone, relaxin, secretin, somatomedin, insulin-like growth factors, adrenocorticotropic hormone, glucagons, cholecystokinin, pancreatic polypeptides, gastrin releasing hormone, coticotropin releasing factors, thyroid stimulating hormones, mono- and poly-clonal antibodies, vaccines, and mixtures thereof. Pegylated versions of proteins, peptides, or other biologic response modifiers are also suitable for incorporation into the compositions of the present invention.

Antiproliferative/antimitotic drugs and prodrugs include natural products such as *Vinca* alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

In certain embodiments, the drug substance is a prodrug or co-drug of an opioid analgesic or an opioid antagonist. Exemplary opioids include morphine and morphine derivatives, such as apomorphine, buprenorphine, codeine, dihydrocodeine, dihydroetorphine, diprenorphine, etorphine, hydrocodone, hydromorphone, levorphanol, meperidine, metopon, o-methylnaltrexone, naloxone, naltrexone, normorphine, oxycodone, and oxymorphone. In other embodiments, the opioid is fentanyl or a fentanyl derivative which can be derivatized to form a prodrug or co-drug, such as beta-hydroxy-3-methylfentanyl. The drug substances may optionally be in pharmaceutically acceptable salt forms.

The term "Iontophoresis" means the migration of ionizable molecules through a medium driven by an applied low level electrical potential. This electrically mediated movement of molecules into tissues is superimposed upon concentration gradient dependent diffusion processes. If the medium or tissue through which the molecules travel also carries a charge, some electro-osmotic flow occurs, However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2-5 mA.

In an embodiment, in iontophoresis, that of enhancing drug delivery through the skin (transdermal iontophoresis), one electrode is positioned over the treatment area and the second electrode is located at a remote site, usually somewhere else on the skin. The return electrode may, for certain applications, be placed elsewhere on the same organ as the iontophoretic delivery electrode. The applied potential for iontophoresis will depend upon number of factors, such as the electrode configuration and position on the tissue, the nature and charge characteristics of the molecules to be delivered, and the presence of other ionic species within the polymer matrix and in the tissue extracellular compartments.

The term "Reservoir" means any form of mechanism to retain an element, compound, pharmaceutical composition, active agent, and the like, in a liquid state, solid state, gaseous state, mixed state and/or transitional state.

In an embodiment, a reservoir may include one or more cavities formed by a structure and may include one or more ion exchange membranes (including electroactive polymer membranes), semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

The term "Iontophoretic system" typically include an active electrode assembly and a counter electrode assembly, each coupled to opposite poles or terminals of a power source, for example a chemical battery or an external power station connected to the iontophoresis device via electrical leads. Each electrode assembly typically includes a respective electrode element to apply an electromotive force and/or current. Such electrode elements often comprise a sacrificial element or compound, for example silver or silver chloride.

In an embodiment, Iontophoretic system may include a provision to isolate sources of moisture from the electrodes and the energy source during storage to optimize storage stability. The inventive system provides a simple user-friendly mechanism for transferring the medicament to be administered and deposits of counterions to the electrodes to activate the device circuit.

In an embodiment, the iontophoretic system is complete, autonomous packaged device that includes all the components necessary for iontophoretic administration, including a device that can be worn; an aqueous anodic matrix; and an aqueous cathodic matrix.

In an embodiment, if the species or active medication to be administered is of a positive charge, it is associated with the anode electrode, if the medication to be administered is of a negative charge, it is associated with the cathodic electrode.

The system includes a power source and at least two electrode assembles. The power source provides an output current that alternates between a maximum current value and a minimum current value, a pair of electrode assemblies. Each electrode assembly is configured to be held in contact with a skin layer of a user. Additionally, each electrode assembly includes an electrode that is coupled to the power source to receive the output current from the power source. At least one of the electrode assemblies in the pair includes a medium that carries an active agent having a charge, the medium being provided on the at least one electrode assembly to enable the output current to repel the active agent into the skin layer for a duration in which the output current has a polarity that is the same as a polarity of the active agent.

In an embodiment, a iontophoretic system may be portable using a sheet mask to be contacted to a user's face comprises a sheet mask with cosmetic fluid applied; an iontophoresor that has a battery providing electric energy and is configured to have one of two electrodes of the above battery electrically connected with a user's skin; and a connection line having one end connected with the sheet mask while the other end is connected with the rest of the two electrodes provided in the iontophoresor and delivering micro-electrical currents of the said battery.

The term "electrode" is a conductor that is used to make contact with a nonmetallic part of a circuit (e.g., a semiconductor, an electrolyte, a vacuum or air). Electrodes are commonly used in electrochemical cells, semiconductors like diodes, and in medical devices. There are two types of electrodes namely reactive and inert electrodes. An inert type does not participate in any reaction while reactive types participate actively in reactions.

In an embodiment, inert electrodes includes for example, not limiting to platinum, gold, graphite (carbon) and rhodium.

In an embodiment, reactive electrode includes for example, not limiting to zinc, copper, lead, and silver.

All electrodes whether inert or reactive comes under the scope of the present invention.

In an embodiment, the relative position of the electrodes can be selected depending on the type of stimulation desired. For example, for Transcutaneous Electrical Nerve Stimulation (TENS) stimulation, the two electrodes should be closer to each other whereas for Electrical Muscle Stimulation (EMS), the two electrodes should be spaced apart. Moreover, the position of electrodes cannot be chosen arbitrarily in that if they are too close, the stimulation may not penetrate enough in the body of the user to achieve the desired stimulation.

In one embodiment, at least one of the electrodes, may include at least one sense electrode or sensor that senses a physiological parameter of patient, such as, but not limited to, electrocardiogram (ECG) parameters, a heart rate, QRS width, atrioventricular (AV) Dissociation, respiration rate, respiratory volume, core temperature, diaphragmatic stimulation such as hiccups, skeletal muscle activity, blood oxygen level, cardiac output, blood pressure, intercardiac pressure, time derivative of intercardiac pressure (dP/dt), electromyogram (EMG) parameters, or electroencephalogram (EEG) parameters. Sense electrodes may be the same electrodes used for delivery of electrical stimulation to patient, or different electrodes.

In an embodiment, present invention may also include at least one sensor in addition to or instead of sense electrodes that may be configured to detect an activity level, motion, posture, intracardiac, intravascular or other pressure within the patient, or another physiological parameter of patient. For example, sensor may comprise an accelerometer. Sensor may generate a signal that varies as a function of at least one physiological parameter of patient. sensing techniques may include one or more algorithms to determine the suitability of each electrode or electrode combination in the stimulation therapy system for sensing at least one physiological parameter.

In an embodiment, sensing physiological parameters may also be accomplished using electrode or sensors that are separate from the stimulation electrodes, e.g., electrodes capable of delivering stimulation therapy, but not selected to deliver the stimulation therapy that is actually being delivered to the patient.

The term "microcontroller" (MCU for microcontroller unit) is a small computer on a single metal-oxide-semiconductor (MOS) integrated circuit (IC) chip. A microcontroller contains one or more CPUs (processor cores) along with memory and programmable input/output peripherals. Program memory in the form of ferroelectric RAM, NOR flash or OTP ROM is also often included on chip, as well as a small amount of RAM.

In an embodiment, microcontrollers may be designed for embedded applications.

In an embodiment, microcontrollers may comprise of various discrete chips.

In an embodiment, microcontroller may also receive physiological signals sensed by selected electrodes or other sensors via switch device. In some examples, microcontroller may receive physiological signals sensed by at least one electrode, which may be used alone or in combination with other electrodes for delivery of medicament. Furthermore, processor may additionally or alternatively receive at least one signal generated by one or more other sensors coupled to processor via a lead or wirelessly, e.g. via communication module.

The term "microcontroller" may be used interchangeably with terms such as "controller", "processor" or "microprocessor" and like.

The term "adhesive" is any non-metallic substance applied to one or both surfaces of two separate items that binds them together and resists their separation. Adhesive, also known as glue, cement, mucilage, or paste. There are a large number of adhesive types for various applications. They may be classified in a variety of ways depending on their chemistries (e.g. epoxies, polyurethanes, polyimides), their form (e.g. paste, liquid, film, pellets, tape), their type (e.g. hot melt, reactive hot melt, thermosetting, pressure sensitive, contact, etc.), or their load carrying capability (structural, semi-structural, or non-structural). Any type of adhesive comes under the scope of the invention. There are adhesives known in the art based on their functionality namely core adhesives add strength to the diaper pad when it is wet; construction adhesives bind the waterproof backsheet to the nonwoven absorbent pads; and elastic adhesives bind legs, waist and lateral panel sheets.

In an embodiment, adhesive is disposed on a backing. The backing may be removable (such as a release liner, including a microstructured release liner or a carrier film) or non-removable such as a polymeric film or a rigid or non-rigid substrate.

In an embodiment, pressure sensitive adhesive (PSA) compositions are well known to those of ordinary skill in the art to possess properties including (1) aggressive and permanent tack, (2) adherence with no more than finger pressure, (3) sufficient ability to hold onto an adherend, and (4) sufficient cohesive strength. Materials that have been found to function well as PSAs include polymers designed and formulated to exhibit the requisite viscoelastic properties resulting in a desired balance of tack, peel adhesion, and shear holding power. The pressure sensitive adhesives are crosslinked prior to embossing. Examples of suitable adhesives include crosslinked acrylics, rubbers, thermoplastic elastomers, silicones, and the like.

In an embodiment, adhesive may be "hot melt adhesive". Hot melt adhesive refers to an article that is solid at room temperature, melts into a liquid by heating, and can achieve adhesion when cooled by applying pressure for several minutes and is to be applied It means an adhesive such as polyolefin block copolymer (SBS, SIS), ethylene vinyl acetate copolymer (EVA) or the like, which is coated thereon.

In an embodiment, adhesive may be "structural adhesive". The structural adhesive is a structure intended to withstand strong forces with high strength, relatively high yield strength, aging resistance, fatigue resistance, corrosion resistance, and stable performance during a specified lifetime. It means an adhesive such as epoxy resin and polyurethane that can be applied to body adhesion.

In a preferred embodiment, the pressure sensitive adhesive is based on at least one poly(meth)acrylate (i.e., a (meth)acrylic pressure sensitive adhesive). Particularly preferred poly(meth)acrylates are derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the glass transition temperature and cohesive strength of the resultant copolymer. Herein, "copolymer" refers to polymers containing two or more different monomers, including terpolymers, tetrapolymers, etc.

In one embodiment, adhesives can be coated using a solvent-based method. For example, the adhesive can be coated by such methods as knife coating, roll coating, gravure coating, rod coating, curtain coating, and air knife coating. The adhesive mixture may also be printed by known methods such as screen printing or inkjet printing. The coated solvent-based adhesive is then dried to remove the solvent. Typically, the coated solvent-based adhesive is subjected to elevated temperatures, such as those supplied by an oven, to expedite drying of the adhesive.

In one embodiment, the thickness of the adhesive layer may be at least about 1 micrometer, at least 5 micrometers, at least 10 micrometers, at least 15 micrometers, or at least 20 micrometers. The thickness is often no greater than about 200 micrometers, no greater than about 175 micrometers, no greater than about 150 micrometers, or no greater than about 125 micrometers. For example, the thickness can be 1 to 200 micrometers, 5 to 100 micrometers, 10 to 50 micrometers, 20 to 50 micrometers, or 1 to 15 micrometers.

In one embodiment, the adhesives may be self-wetting and removable. The adhesives exhibit great conformability permitting them to spontaneously wet out substrates. The surface characteristics also permit the adhesives to be bonded and removed from the substrate repeatedly for repositioning or reworking. The strong cohesive strength of the adhesives gives them structural integrity limiting cold flow and giving elevated temperature resistance in addition to permanent removability.

In one embodiment, adhesives may be viscoelastic or elastomeric adhesives, rubber based adhesives, silicon based adhesives. Viscoelastic or elastomeric adhesives further include elastomeric polyurethane or silicone adhesives and the viscoelastic optically clear adhesives CEF22, 817x, and 818x, all available from 3M Company, St. Paul, Minn. Other useful viscoelastic or elastomeric adhesives include PSAs based on styrene block copolymers, (meth)acrylic block copolymers, polyvinyl ethers, polyolefins, and poly(meth) acrylates.

The term "physiological parameters" Exemplary physiological parameters include, but are not limited to, subject body temperature, subject heart rate, subject heart rate variability, subject blood gas levels, subject metabolic rate, subject respiration rate, subject blood analyte levels, subject blood pressure, subject pulse pressure, etc.

In an embodiment, the invention measures a value of a physiological parameter for a subject at a selected state (e.g., state of peak metabolism, state of lowered metabolism, state of rest, etc.), includes obtaining, via a device attached to the subject, a value of the physiological parameter of the subject at a particular time-of-day, and applying a time-dependent relationship function to the obtained physiological parameter value via at least one processor to determine a value of the physiological parameter at the selected state.

The term "software" is a collection of instructions and data that tell the computer how to work. In an embodiment, software allows for the real-time programmatic control of computer programs implemented using different GUI technologies, executing on one or multiple computing devices, and/or executing on one or multiple virtual machines.

The term "Bluetooth Low Energy" (BLE) is a wireless personal area network (WPAN) technology designed and marketed by the Bluetooth Special Interest Group (Bluetooth SIG) aimed at novel applications in the healthcare, fitness, beacons, security, and home entertainment industries. It is independent of Bluetooth BR/EDR and has no compatibility, but BR/EDR and LE can coexist. The original specification was developed by Nokia in 2006 under the name Wibree which was integrated into Bluetooth 4.0 in December 2009 as Bluetooth Low Energy. All wireless personal area networks (WPANs) including rDA, Wireless USB, Bluetooth or ZigBee comes under the scope of the present invention.

The term "sensor" is a device, module, machine, or subsystem whose purpose is to detect events or changes in its environment and send the information to other electronics, frequently a computer processor. A sensor is always used with other electronics.

The term "biosensor" is an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts with, binds with, or recognizes the analyte under study. The biosensor may include pulse oximeter, heart rate sensor, ECG sensor, skin sensors, temperature sensor, blood pressure sensor, impedance sensor etc. According to one embodiment, all types of biosensor comes under the scope of the present invention.

The term "tactile sensor" is a device that measures information arising from physical interaction with its environment. Tactile sensors are generally modeled after the biological sense of cutaneous touch which is capable of detecting stimuli resulting from mechanical stimulation, temperature, and pain. Tactile sensors are used in robotics, computer hardware and security systems. A common application of tactile sensors is in touchscreen devices on mobile phones and computing.

The term "blood pressure sensor" is a non-invasive sensor designed to measure human blood pressure. It measures systolic, diastolic and mean arterial pressure utilizing the oscillometric method.

The term "heart rate sensor" measures your heart rate in Beats per Minute using an optical LED light source and an LED light sensor.

The term "temperature sensor" is an electronic device that measures the temperature of its environment and converts the input data into electronic data to record, monitor, or signal temperature changes.

The term "non-bio sensor" is defined as a senor that does not sense a biological or physiological parameter.

The term "opioid" are a class of drugs naturally found in the opium poppy plant. Some prescription opioids are made from the plant directly, and others are made by scientists in labs using the same chemical structure. Opioids are often used as medicines because they contain chemicals that relax the body and can relieve pain. Opioids include the illegal drug heroin, synthetic opioids such as fentanyl, and pain relievers available legally by prescription, such as oxycodone (OxyContin®), hydrocodone (Vicodin®), codeine, morphine, and many others.

The term "non-opioid drug" is a drug that is not an opioid.

The term "opioid agonist" are drugs that bind to opioid receptors and undergo significant conformational change to produce maximal effect.

The term "opioid agonist" may be interchangeably used as "opioid".

Opioid agonist may be full or partial. Full agonists bind tightly to the opioid receptors and undergo significant conformational change to produce maximal effect. Examples of full agonists include codeine, fentanyl, heroin, hydrocodone, methadone, morphine, and oxycodone.

In an embodiment, partial agonists cause less conformational change and receptor activation than full agonists. At low doses, both full and partial agonists may provide similar effects to their full agonist cousins. However, when the dose of partial agonists increases, the analgesic activity will plateau, and further increases in doses will not provide additional relief but may increase the adverse effects. Examples of partial agonists include buprenorphine, butorphanol, and tramadol. There are mixed agonists/antagonists, which demonstrate varying activity depending on the opioid receptor but also varying on the dose. Examples include buprenorphine, butorphanol, nalbuphine, and pentazocine.

Opioid analgesics which could also be useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the like.

In certain preferred embodiments, the opioid agonist or analgesic is selected front from the group consisting of hydrocodone, morphine, hydromorphone, oxycodone, codeine, levorphanol, meperidine, methadone, oxymorphone, dihydrocodeine, tramadol or salts thereof; or mixtures thereof. In certain preferred embodiments, the opioid agonist is hydrocodone.

The term "opioid antagonist" is a receptor antagonist that acts on one or more of the opioid receptors. Naloxone and naltrexone are commonly used opioid antagonist drugs which are competitive antagonists that bind to the opioid receptors with higher affinity than agonists but do not activate the receptors. This effectively blocks the receptor, preventing the body from responding to opioids and endorphins. Some opioid antagonists are not pure antagonists but do produce some weak opioid partial agonist effects, and can produce analgesic effects when administered in high doses to opioid-naive individuals. Examples of such compounds include but not limited to nalorphine and levallorphan.

In an embodiment, opioid antagonist includes but not limited to μ-opioid receptor (MOR) antagonists or inverse agonists. Many of them also bind to the κ-opioid receptor (KOR) and/or δ-opioid receptor (DOR) where they variously behave as antagonists and/or agonists. List of opioid antagonist includes but not limited to Naloxone, Naltrexone, Nalmefene, Samidorphan or like.

In an embodiment, opioid antagonists include but not limited to buprenorphine, cyclazocine, cyclorphan, naloxone, N-methylnaloxone, naltrexone, N-methylnaltrexone, nalmefene, 6-amino-6-desoxo-naloxone, levalorphan, nalbuphine, naltrendol, Examples include naltrindole, nalolphine, norbinaltolfimine, oxylorphan, pentazocine, piperidine-N-alkylcarboxylate opioid antagonists, and opioid antagonist polypeptides. A particularly preferred opioid antagonist is naloxone or a derivative thereof (eg 6-amino-6-desoxo-naloxone).

The term "activated charcoal" is a form of carbon processed to have small, low-volume pores that increase the surface area available for adsorption or chemical reactions.

The term "overdose" is a biological response to when the human body receives too much of a substance or mix of substances. People can overdose on illicit drugs, alcohol, prescription medications, and many other substances.

The term "cathode" is the negatively charged electrode and attracts cations or positive charge. It is the source of electrons or an electron donor.

The term "anode" is the positively charged electrode and attracts electrons or anions. It is a source of positive charge or an electron acceptor.

The term "system" or "device" is defined by a physical hardware or an equipment or a thing made or adapted for a particular purpose. In an embodiment, the patch is a device as it is intended for a particular purpose.

The term "biodegradable" is defined as a material capable of biodegradation. Biodegradation is the breakdown of organic matter by microorganisms, such as bacteria and fungi.

The term "skin" as used herein is the layer of usually soft, flexible outer tissue covering the body of a vertebrate or invertebrate animal, with three main functions: protection, regulation, and sensation.

The term "semipermeable membrane" is a type of biological or synthetic, polymeric membrane that will allow certain molecules or ions to pass through it by diffusion—or occasionally by more specialized processes of facilitated diffusion, passive transport or active transport. The rate of passage depends on the pressure, concentration, and temperature of the molecules or solutes on either side, as well as the permeability of the membrane to each solute. Depending on the membrane and the solute, permeability may depend on solute size, solubility, properties, or chemistry.

The term "energy storing device" is a device that stores energy is generally called an accumulator or battery. The battery could be rechargeable battery such as but not limited to Lead-acid battery, Nickel-cadmium battery (NiCd), Nickel-metal hydride battery (NiMH), Lithium-ion battery, Lithium-ion polymer battery. The batter could be a flow battery.

Waterproofing is the process of making an object or structure waterproof or water-resistant so that it remains relatively unaffected by water or resisting the ingress of water under specified conditions. The term "water proof safeguards" or "waterproofing agent" or like refers to are sealant additives and/or resins that repel water and prevent damage to the underlying sealed substrate.

In an embodiment, waterproofing agent may include but not limited to application of beeswax, waterproofing spray, or mink oil, lignin coating, ethylene propylene diene monomer EPDM rubber, hypalon, polyvinyl chloride etc.

The term "app" as used herein is an application (app), application program or application software is a computer program designed to help people perform an activity. Depending on the activity for which it was designed, an application can manipulate text, numbers, audio, graphics, and a combination of these elements. Some application packages focus on a single task, such as word processing; others, called integrated software include several applications. Apps could also build for mobile platforms.

The present invention relates to transdermal delivery of plurality of therapeutic drugs by iontophoresis and systems comprising thereof. More specifically, this invention relates to the transdermal delivery of opioid and opioid antagonist.

An embodiment of invention relates to a transdermal drug delivery system in the form of a patch comprising a cartridge which comprises a drug, a sensor, an active delivery pad. The active delivery pad comprises an electrode for delivery of the drug into a tissue via iontophoresis, a power source of electrical energy connected to the electrode, a microcontroller configured to control a release of the drug. Further, the said patch is attached to the tissue via an adhesive pad and the top of patch is covered with a cover sheet.

In an embodiment, the sensor could be biosensor or non-biosensor. The biosensor is configured to detect a physiological parameter and the non-biosensor is configured with a software to control working of the patch.

The present invention provides a convenient, comfortable, and safe solution for any person who requires a drug prescription. The system advantageously utilizes physiological conditions of user to automatically give at least one drug or medicine when certain criteria are met. The system has a multitude of safeguards to prevent possible misuse of the medication within the patch.

In an embodiment, the present invention system has a security feature that would prevent unauthorized access to the stored drugs. A biosensor to deter overdosing, a release button which can triggered manually for release of drugs. The scheduled drug dosing could be controlled through the mobile or web application.

In an embodiment, the patch has multitude of safeguards to map out any issues that could go wrong with the with the patch, and to solve those issues. A software can send alert to a user on working condition of patch including an overdose of the drug, an accidental loss of the patch, a defunct power source, an empty cartridge or any combination thereof.

In one aspect, the system starts releasing or stop releasing of drug when software connected to the system sends an alert to a user on a working condition of patch including an overdose of the drug, an accidental loss of the patch, a defunct power source, an empty cartridge, or any combination thereof.

In another aspect of automatic system is receiving a physiological parameter indicative of a medical state of a person and send a signal to start/stop release of a drug. Furthermore, patient need not be bothered about his/her prescription as the patch will automatically deliver the medication through scheduled dosing. Whether the patient has a history with drug-abuse or not, this medical patch encompasses various safeguards and design-features, which makes it the most convenient and user-friendly drug delivery system. The system provides a release button for release of drug which can be regulated manually or automatically.

In an embodiment, sensors and the iontophoresis electrode help to transport drug to the patient.

The invention is the first opioid solution that introduces an autonomous naloxone supply which counteracts the negative effects of a possible opioid overdose. It is also the first opioid drug delivery system which is fully autonomous and can be controlled from a remote app on a mobile device or laptop. Additionally, the use of a password to limit the patient's access to the opioid medication within the patch is a completely new feature which has not been introduced in any other medical patch.

In one embodiment, the patch of transdermal drug delivery system comprises a first cartridge which comprises a first drug and a second cartridge comprises a second drug. Further, the first cartridge and second cartridge are separated from each other.

In one embodiment, the cartridge is configured to hold a plurality of drug forms, wherein cartridge is reusable.

In an embodiment, the first and second cartridges are separated from one another.

In another embodiment, the drug in cartridges comprises of an opioid drug, an opioid antagonist. Further, the opioid antagonist comprises of Naloxone. In an embodiment, the present system has a) has a naloxone compartment b) releases opioid and naloxone using iontophoresis. The present system is the only biodegradable opioid patch in the market.

In an embodiment, opioid application system connected to an app either on mobile or any other similar electronic device. In an embodiment, the scheduled opioid dosing is controlled through the mobile application, the autonomous naloxone drug supply in cases of overdose, the biological indicators and the corresponding medical sensors to track them, and the use of active pads with iontophoresis to deliver the drug.

In an embodiment, opioid antagonist and opioid may be paired to create a solution to accidental overdose of opioid.

In an embodiment, Naloxone paired with an opioid create a solution to accidental overdoses and to curb drug usage by making it harder to access the actual opioid.

In an embodiment, the biosensor could be but not limited to blood pressure sensor, a temperature sensor, and a heart rate sensor, a tactile sensor and the non-biosensor comprises a BLE sensor.

In an embodiment, the electrode comprises of zinc and silver chloride electrode.

In one embodiment, the adhesive pad of transdermal drug delivery system comprises a substrate including an activated charcoal and an adhesive material comprising a Polycarbonate adhesive.

In an embodiment, the sheet of transdermal drug delivery system is made up of lignin.

In an embodiment, transdermal drug delivery system comprises of the release of the drug starts on a signal and the signal is regulated manually comprising a release button/app or automatically based on physiological condition of a user.

In an embodiment, transdermal drug delivery system comprises of the software which sends an alert to a user on a working condition of the patch.

In another embodiment, transdermal drug delivery system where the working condition of the patch includes an overdose of the drug, an accidental loss of the patch, a defunct power source, an empty cartridge, or any combination thereof.

In an embodiment, the patch of transdermal drug delivery system further comprises a first system to replace the power source and/or to recharge the power source, and a second system to refill the cartridge.

In an embodiment, the patch of transdermal drug delivery system has any shape or any size. Shape may include any geometric shapes but not limited to rectangular, square, circle, hexagonal, triangle etc.

In another embodiment, the patch is configured with a software to alert the user of the patch about a working condition of the patch; wherein the patch further comprises a non-biosensor comprising a BLE sensor.

In an embodiment, the source of electric power comprises a battery and the battery comprises a coin battery, or a rechargeable mini battery.

In an embodiment, top of the patch comprising the source of electric power, the biosensor, cartridges. The top part of the patch is covered with a cover sheet.

In an embodiment, the adhesive layer comprises a substrate comprising an activated charcoal, and an adhesive material comprising a polycarbonate adhesive.

In another embodiment, a method to regulate release of a drug comprises of attaching a patch, sending a signal to start an electric current flow, transferring of the drug by an iontophoretic transdermal delivery system, and the release of the drug is controlled by the microcontroller.

In an embodiment, the electrodes comprise wires that are round, circular and/or coated wires.

In an embodiment, the wires are coated with zinc chloride or silver chloride, and wherein an anode comprises the zinc chloride and a cathode comprises the silver chloride.

In an embodiment, the first reservoir and/or the second reservoir comprises a cartridge that is configured to hold a plurality of drug forms.

In an embodiment, the cartridge is partially reusable or fully reusable.

In an embodiment the first reservoir and the second reservoir are separated from one another.

In an embodiment, first reservoir comprises an opioid, an opioid agonist or a partial opioid agonist.

In an embodiment, the second reservoir comprises an opioid antagonist.

In an embodiment, the source of electric power comprises a battery.

In an embodiment, the battery comprises a non-rechargeable battery or a rechargeable battery.

In an embodiment, the system comprises a biosensor coupled to the microcontroller to verify a medical characteristic of the patient prior to delivery of the opioid, the opioid agonist or the partial opioid agonist.

In an embodiment, the microcontroller is adapted to analyze the medical characteristic of the patient to determine a symptom associated with an opioid overdose in the patient.

In an embodiment, the symptom corresponds to a decrease in respiratory rate, a decrease in heart rate, a decrease in blood pressure, deviations from normal body temperature, passing out or an unresponsive loss of consciousness, skin color changes, abnormal breathing, fast, slow or irregular breathing, severe chest pain, seizures, severe headaches, difficulty in breathing, delirium, agitation, and/or anxiety.

In an embodiment, the microcontroller is further configured to send an alert or notification wirelessly upon detection of the symptom.

In an embodiment, the biosensor comprises a pulse oximeter, a heart rate sensor, an ECG sensor, a skin sensor, a temperature sensor, and/or a blood flow sensor.

In an embodiment, the adhesive layer comprises a biodegradable polycarbonate.

In an embodiment, a cover sheet covering the patch.

In another embodiment, the patch comprises a shape and a size.

In an embodiment, the patch system is a reusable self-administrable opioid and Naloxone patch designed to be biocompatible comfortable and cost effective.

In an embodiment, the system is a reusable self-administrable opioid and naloxone patch designed to be biocompatible, comfortable, and cost-effective. The system includes two separated cartridges, both of which are refillable. The separation allows for a dual drug delivery system. Specifically, the system designed for an agonist and an antagonist, though it can be applied for two drugs in general as well.

In an embodiment, any microcontroller can be used. Arduino, for example, but Raspberry Pi is also a strong example.

In another embodiment, any active electrode material may be used for electrodes. Zinc and silver chloride, for example, can be used, but aluminum electrodes can also be used.

In terms of the adhesive, any skin adhesive would suffice. Biodegradable polycarbonate adhesive is preferred, but any form of skin adhesive (3M) can be used.

In an embodiment, the patch material can be made of any biodegradable material; in this case, bamboo fibers and activated charcoal are used. The patch, however, can be made of any biodegradable material.

In terms of power/energy source, the patch operated by an electric current or any electrodes can be used, as long as they have the capacity to do so like zinc and silver electrode.

In another embodiment, for cartridge positioning and orientation, any conductive material for an electrical current can be used, and any modification can be made. However, it can be vertically dominant or horizontally dominant, and it can also be modified to be positioned in the left center or right center, but the general positioning of it will always be the upper arm part.

In an embodiment, any modification to sensor positioning can be made; it can be positioned vertically, horizontally, if the only restriction is that it fits inside the design interior.

In the case of waterproof safeguards, lignin coating may be used, but any coating that renders anything waterproof and guarantees that water cannot kill or harm the device is used. In terms of pad placement or orientation, it doesn't matter whether it's vertical, horizontal, left middle, or right; what matters is that the whole patch is distributing the drugs on the arm section.

As shown in FIG. 1 the system is a reusable self-administrable opioid and naloxone patch designed to be biocompatible, comfortable, and cost-effective. The device includes two separated cartridges, both of which are refillable. The separation allows for a dual drug delivery system. To go into specifics, the FIG. 1 was built for an agonist and an antagonist, though it can be applied for two drugs in general as well. As shown in FIG. 1 the patch split into three different parts. Cartridges on either side and in the center, there is a primary battery and Controller.

Figure 2:
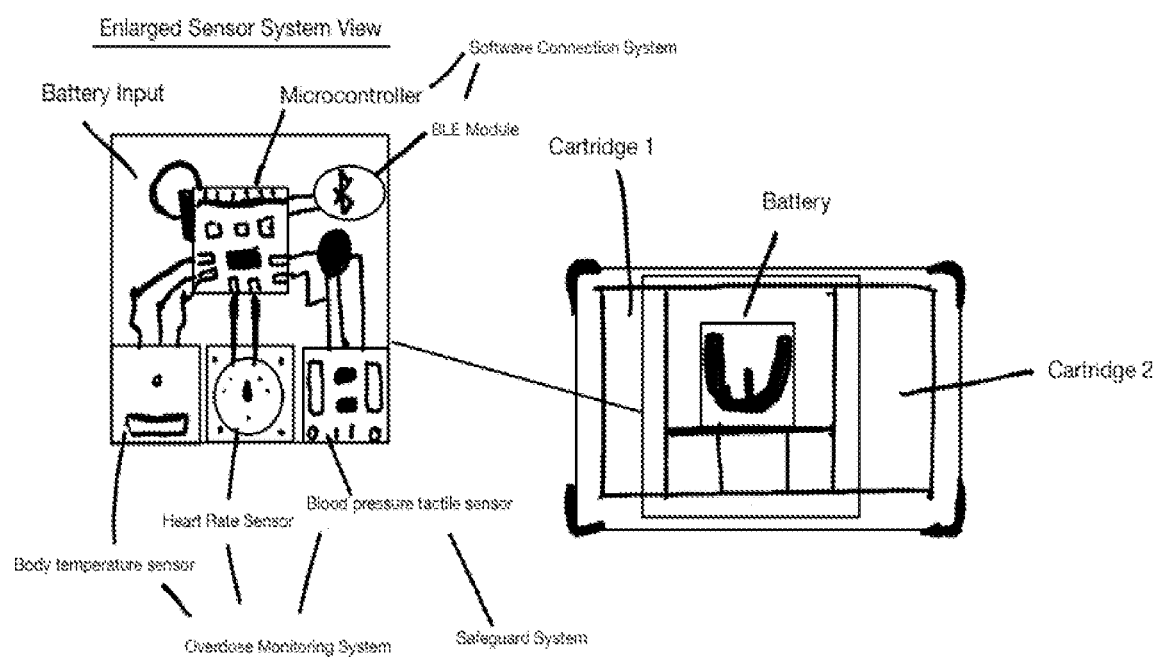
FIG. 2 illustrates a top aerial view of the patch system (Left) is an enlarged view of sensors. A sensor could be body temperature sensor, heart rate sensor, blood pressure tactile sensor, battery input, microcontroller, BLE module, software connection system. (Right) is a top view of a self-contained iontophoretic drug delivery system which includes cartridges and battery according to one of the embodiments.

In an embodiment, FIG. 2 illustrates a top aerial view of the patch system. In right of FIG. 2, the batteries are horseshoe shaped (black colored). There are two cartridges one is one side and the other cartridge on other side. In the center, microcontroller, battery and sensors are present.

Figure 7:
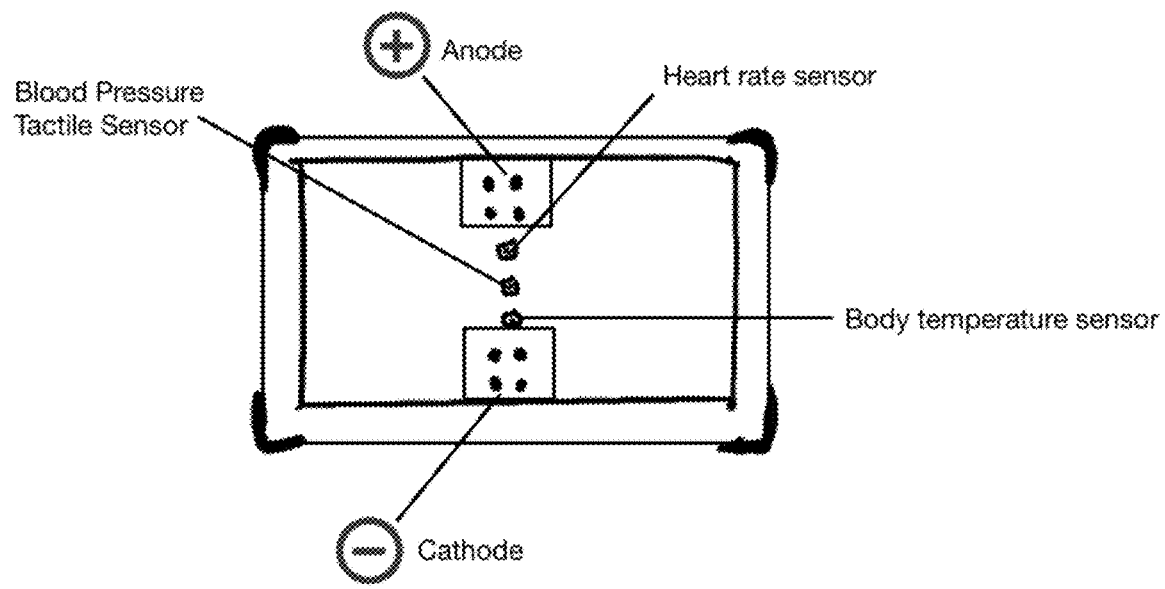
FIG. 7 illustrates active pad which includes blood pressure tactile sensor, body temperature sensor, heart rate sensor, anode and cathode according one of the aspect of the present invention.

In FIG. 1, the outermost part of the patch on which the dual delivery system reside is made up of bamboo fiber plus activated charcoal. However, it can be made of any biodegradable material, for example include, without limitation, alginate, chitosan, cotton, wool, collagen, elastin, silk, keratin, gelatin, polyamino acids, polysaccharides (e.g., cellulose and starch), proteins, natural rubber, pectin, chitin, polyhydroxyalkanoates and copolymers thereof. In an embodiment, system also comprise of delivery pad, as shown in FIG. 7, and at the bottom of the patch that can be made out of embedded zinc and silver chloride electrodes. The active delivery pad includes electrodes. In an embodiment, electrodes could be active, moderately active or passive. Additionally, it comprises of a semi permeable membrane and a saline solution housed in the bottom of the patch. Additionally, system have a battery that can be replaceable and/or rechargeable, the battery could be any such as but not limited to a lithium-ion battery.

The system also consists of a malleable plastic film, which is a thin plastic film on top of the patch, which is translucent.

The patch system has the adhesive which is any biodegradable polycarbonate to make it comfortable and convenient for user. Another examples of adhesive that may be employed but not limited are polyurethane adhesives, pressure-sensitive adhesive such as an acrylic pressure-sensitive adhesive or a polyether pressure-sensitive adhesive, UV-cure adhesives, adhesives containing acrylates or methacrylates etc.

The system also has microcontroller, which can be any microcontroller and wiring for that respective microcontroller. In an embodiment, the microcontroller is Arduino.

Left side of FIG. 2 illustrates enlarged view of sensors. At the top microcontroller is there. There is a battery input which feeds into the microcontroller and the battery is placed on top of the microcontroller. In the aerial view, microcontroller 'Arduino' has a wiring which connects to every sensor. Bluetooth low energy module, which is also connected to the microcontroller. On the leftmost side, at the bottom, battery, temperature sensor, heart rate sensor. and blood pressure tactile sensor are present. The black dot or black section next to the microcontroller is the tactile sensor.

All of these sensors will connect directly to the skin.

In an embodiment, as seen in FIG. 7, the sensors are connected through dots between the cathode and the anode. The body temperature sensor, heart rate sensor, blood pressure, tactile sensor fall under the overdose monitoring system, the tactile sensors, part of the safeguard system, and the microcontroller and the BLE module themselves are part of the software connection system. So this enlarge sensor system, there's no exact way they have to be placed, as long as they all connect to the microcontroller, there's no specific order on the main thing of this sensor system is that all of these components exist within the center part of the patch, all of them are wired correctly to the microcontroller. The three sensors have direct access to the skin through the three dots as mentioned in FIG. 7.

Figure 3:
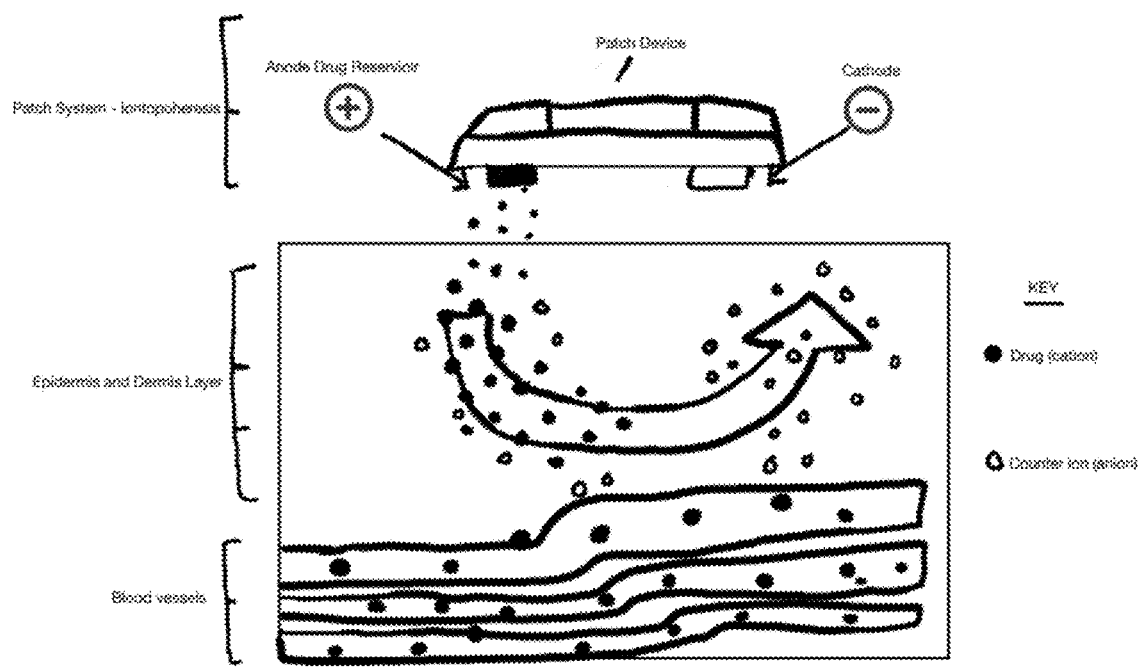
FIG. 3 is an illustration of iontophoretic system for transdermal drug delivery of drug, according to one or more embodiments.

In an embodiment, Iontophoresis is used in device. Iontophoresis procedure is a harmless electrical current to send particles through the skin barrier by electrophoresis and electro osmosis. FIG. 3 illustrates iontophoretic system for transdermal drug delivery of active drug that uses a harmless electrical current to send particles through the skin barrier, by electrophoresis and electroosmosis; wherein the electric field generated by the system which increases the permeability of the epidermis, making the drug delivery process more efficient; wherein this whole process is start with the app, controlled by microcontroller and charged by coin battery; wherein the medication introduced in the body with 10 minute doses according to the aspect of the invention.

The electric field generated by device increases the permeability of the epidermis making the drug delivery process more efficient. This will be controlled by the microcontroller. And the battery powered current is deployed by the app. The medication will be introduced into the body within 10 minute doses.

In an embodiment, the system specifics about the drug electrical charge used to deploy the opioid through iontophoresis. The typical dosage is around 40 milli amperes per minute and delivered in doses of 10 minute intervals or 20 minute intervals and specifically for each of them for the electrodes that will be for milli amperes for each 10 minute interval or two milli amperes for each of these 20 minute intervals. As a result, the average rate of the opiate delivery is dependent on the actual drug constants.

In an embodiment, the system accommodating for a drug called fentanyl. However, drug may be any kind of opioid using the formula displayed at the bottom of the slide. The rate of delivery is determined by different constants such as the Faraday's constant, the actual electrical charge number of the opioid itself and constants such as those that determine. Finally, the actual rate of delivery that the patch can deliver to the body.

In an embodiment, release rate of the drug is $R\_d=(t\_d\ IM\_d)/(z\_d\ F)$ Where Rd=rate of transdermal delivery of the drug, td is the transport number or a fraction of charge that is carried by an ion of the drug, I is the current, Md is molecular weight of the ion of the drug, zd is the valence of the ion of the drug, F is Faraday's Constant.

In another embodiment, iontophoretic delivery system wherein, the dose is controlled by the amount of electrical current and is fixed to not exceed 40 µg, the dosing interval is 10 minutes, and each dose is a 10-minute infusion. Drug delivery begins when the electrical current is activated by pressing the dosing button. The current can be activated and stopped on command.

Naloxone is a medication which is designed to rapidly reverse any opioid overdose effects. It is an opioid antagonist, which means it binds to opioid receptors and can reverse and block the effects of opioids. The present system used Naloxone, but other drugs and other antagonists could be used instead. Naloxone stored in half of the patch, which is that blue section blue part of the patch system as shown in FIG. 1.

The overarching steps for naloxone release, the patch on your skin can use the in-built sensors to detect abnormalities. This is measured through blood pressure and any deviations from the normal body temperature and pulse. If you are pass out or become unresponsive or your skin color changes, or if there are fast or irregular polls, then these bio indicators do indicate an overdose according to the sensors, then the user will be alerted through the app and naloxone will be released, and the user's doctor and any emergency medical services will be notified. For example: there is a microchip that monitors blood pressure. So if there's any spike in blood pressure that occurred using ionic resists, no oxygen will be released and the current to the opioid would be shut off.

Safeguards are the biggest part of patch. The first of it being water damage, meaning that this patch is waterproof And this comes from a lignin coating. lignin is a plant-based coating basically which can be applied to this patch system and it will waterproof the plastic malleable film or the outside layer of this patch. Additionally, if the patient does overdose, the patch has an naloxone release feature to counteract overdose. If there is a battery shortage, the patch can employ different options such as either make the battery rechargeable, or the battery could be replaced as it is a simple coin battery located on the external part of the patch, The patch has another safeguard for the naloxone malfunction. The bio indicators track the patient's vitals. And if these bio indicators indicate that the patient is in need of medical services, then the authorities are alerted. Furthermore, the system has misactivated the app or the iontophoresis mechanism, especially for opioids. The machine can activate Naloxone if the opioid is mistakenly released. Both the patient and the doctor can use a manual app override in the method.

Furthermore, the device has a detachment feature, which ensures that if the patch falls off, the tactile sensor, which is combined with the blood pressure sensor, will lock the patch through the app. Additionally, the system has password protection which ensures that the doctor can allocate a password to the patient, and only if that password is entered can the dosing process start. This is also controlled through the app and software. When a patch puncture or the cartridges themselves begin to leak the fluid medication, the doctor is alerted.

Safeguard includes a wide array of sensors. These sensors are categorized into three different systems. First one is the overdose monitoring system, which includes a heart rate sensor, a blood pressure sensor and a body temperature sensor. These three allow bio indicators to be sent to the app which can then be analysed to determine whether iontophoresis is needed to allow Naloxone to reach the body in case of an overdose.

The second safeguard system is a tactile sensor which will cause the patch to lock instantly, resulting in a locked patch. A locked patch is one in which iontophoresis has been switched off entirely and getting drugs from inside the patch through iontophoresis or the password is no longer possible because the password has been disconnected. The tactile sensor would also be connected to the blood pressure sensor as they are able to monitor the same thing together.

The third system is the software connection system which consist of a BLE module and the microcontroller that are both placed in the center of the patch. The BLE module attaches the patch to the app, allowing details to be exchanged with the doctor and patient. All of the sensors are managed by the microcontroller, which also groups all of the data together.

The Bluetooth module is completely paired to the mobile application that can be easily accessed by the user and the mobile application allows the user to view data, essentially any vital data collected by the patch. The mobile screen will be able to display heart rate, blood pressure, body temperature, or any other metrics that the sensors are collecting, and it will always give certain Boolean values like whether it is paired or not, whether it's locked or not, and whether it's delivering opioids at the moment or not, as well as displaying battery level, so the user will always know if they need to change or recharge the coin battery. The cloud services will be used for data transmission and storage, and in this case, AWS services are available. Overall, the system will save and track sensor data using tools like the S3 bucket and the EC2 instance, as well as ensure that the database can always be accessed and transmitted to any doctor-side database. The mobile app will be coated in anything specifically React Native. It will essentially have some kind of framework back end tied to this AWS setup to ensure that the data can be viewed on both sides, both the user spectrum and doctor spectrum. The app also integrates in app messaging between the user and their doctor. SMTP incorporation, or Quick Mail Transfer Protocol, is used in this case and they can still make sure they are in touch in case of an emergency or something similar.

Figure 4:
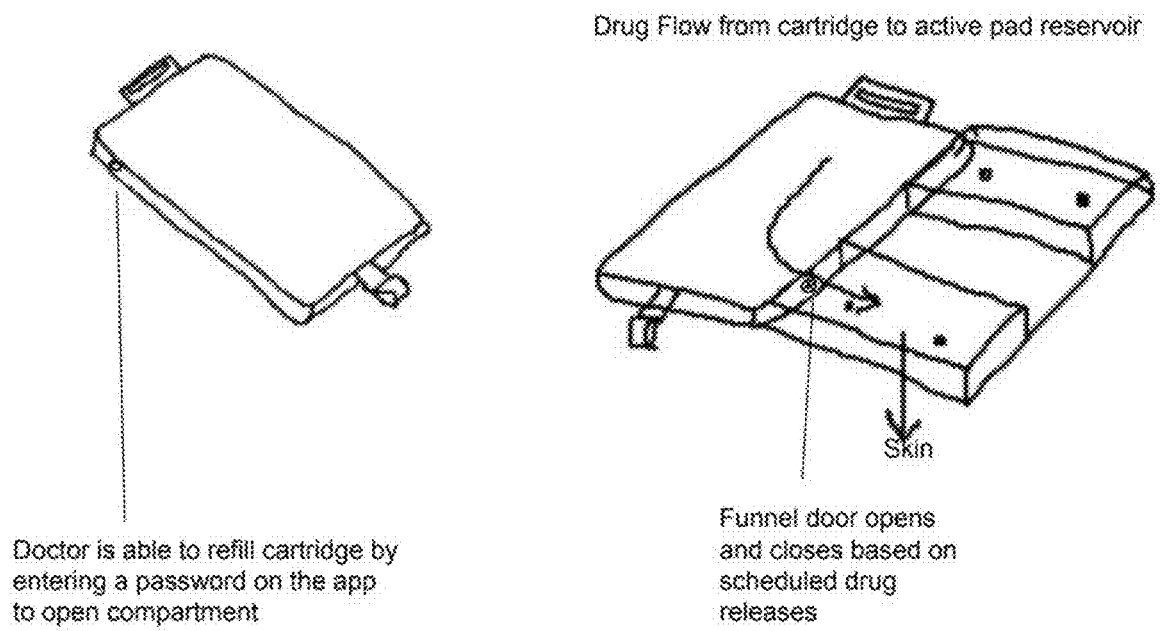
FIG. 4 show view of cartridge in the patch and drug flow from cartridge to active pad reservoir.

In an embodiment, FIG. 4 (left) shows cartridge which can refill by doctor on entering a password on the app to open compartment according to one of the aspect of the invention. There are two doors that are opening and this is where these doors would open based on when the drug is scheduled to release. Moreover, this depends on the user and what the doctor puts in and prescribes for a specific user. These doors will open according to the schedule, allowing the drug to flow into the reservoir and then be released.

In an embodiment, FIG. 4 (right) illustrates drug flow from cartridge to active pad reservoir wherein opening and closing of funnel door based on scheduled drug releases according to one of the aspects of the invention. The Figure illustrate the bottom view of the patch external above the skin patch system and the top layer uses iontophoresis including the anode, drug reservoir, and the cathode to deliver the drug cations, which shown as black dots into the epidermis and dermis layer of the skin in the Figure and all flow in the direction of the arrow. Many of these drug or cations will enter the blood vessels so that the drug can have its effects on the body and the counter ions will flow in the opposite direction. The patch system on top has the sensors and the cartridges and, on the bottom, have double active pads or four cathode and anode. However, it is a pair of four and as shown in the figure two on the left side, two on the right side, two of which are for the anode and cathode of the opioid agonist and two of which are for the opioid antagonist.

In an embodiment, gate mechanism is present for closing and opening of doors. Two sets of passwords are accessible to the doctor and the recipient or patient. The password that the user would put into their app would be to start the AI on top races into their patch, when the patch is already on their body, the doctor he would put in he or she would put in the password into the app only when it would require a refill, or when the patch needs to be reset, which gives the doctor privilege over the opioid distribution in case of any type, which would prevent any type of abuse from happening on the patient side. It's all connected to the microcontroller and that goes back to the app and the password. So that's how, gate mechanism occurs.

Essentially, the microcontroller would be controlling the doors themselves and it will be sending basically, electricity to whatever component needs it whenever an event happens. Whenever, drugs need to be released into the body, voltage would be sent to the actual components, and a technology like push buttons that can be incorporated with any kind of microcontroller. Small push buttons work already by themselves and open and close the doors. This event would be controlled through the microcontroller itself through the voltage that's being sent whenever an event happens. In that case, the event is whenever the actual drug needs to be deployed, or whenever the password is inputted or whenever.

In an embodiment, if a patch is activated prior to password authentication, the switch can be controlled manually or via app.

In another embodiment, Heart rate is tracked, so if it is rising too fast, naloxone will automatically be deployed.

In an embodiment, if an accident occurs or if a user takes off the patch manually, an alert is sent to the app and a caretaker/doctor.

In an embodiment, taking the patch off is not life-threatening, so a large safeguard does not have to be implemented.

In an embodiment, the patch has a tactile sensor which simply alerts concerned parties if the patch is removed.

In an embodiment, Iontophoresis switch is only activated once an auto-generated password is texted to the user and prevents multiple patches to be used at once.

In an embodiment, If the opioid chamber is empty, an automated message sent to the doctors/caretaker.

In an embodiment, whenever you open the door, you fill it up in the cathode and from cathode to the skin, there is some rate but it's limited by what's getting pulled in. If it's an osmosis process, it's pulled into the skin and that's how the process is controlled.

In an embodiment, plurality of drugs can be released in the form of liquid.

In an embodiment, the system does not require needles or any type of any type of penetration into the skin layer, what the exact drug would only move into the body through the anode side, the cathode side is just to balance out the electrical field with within between the skin barrier.

In an embodiment, the system is like a push pull with two drugs system. The system introduces (pushes) first drug into the body, when the first drug is overdosed, the first drug is pulled by introducing a counter antagonist.

Figure 5:
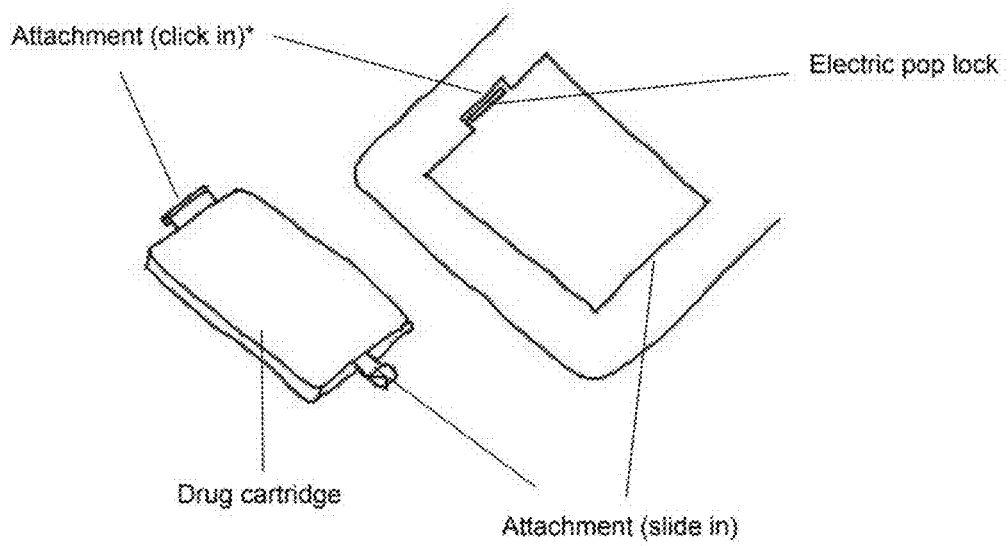
FIG. 5 illustrates attachment and detachment of cartridges from the pouch according to one of the aspects of the invention.

In an embodiment, FIG. 5 illustrates how the cartridge would attach or detach from the pouch. there is an electric pop lock, basically it is a socket that would pop up when the cartridge should not be in the patch. This is if the doctor put the password in the app to lock it, then the pop would, the lock would pop up. And when they put the password in the app, then it would unblock the socket, and it opened the lock to allow for the cartridge to be added into the patch or to put a new cartridge into the pouch. As a consequence, they all bind to the patch using the same mechanism. However, if anyone wishes to avoid this from occurring, there is a system in place where the password can be inserted into the app to lock the socket.

The electric pop lock socket will be blocked at all times, unless the doctor puts the password in the app which when unblocks the socket and opens the lock to allow for an old cartridge to be removed or a new cartridge to be added.

Figure 6:
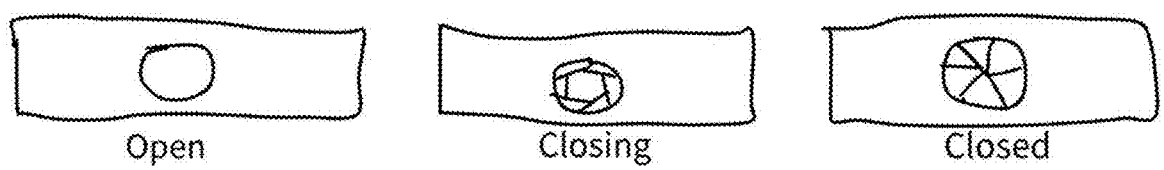
FIG. 6 illustrates opening and closing of funnel door depending on amount of time drug is being transferred according to aspect of the present invention.

In an embodiment, FIG. 6 illustrates the opening and closing of funnel door depending on amount of time drug is being transferred wherein microcontroller sends electricity to a motor to trigger the opening and closing of the door according to aspect of the present invention.

In an embodiment, FIG. 7 illustrates active pad of the system where three dots or squares in the middle of the diagram indicates heart rate sensor at the top, blood pressure tactile sensor in the middle and body temperature sensor right above the cathode. Fig further showing cathode and anode which will be delivering the drugs through iontophoresis. Cathode is negative and anode is positive as can be seen in the Figure.

Figure 8:
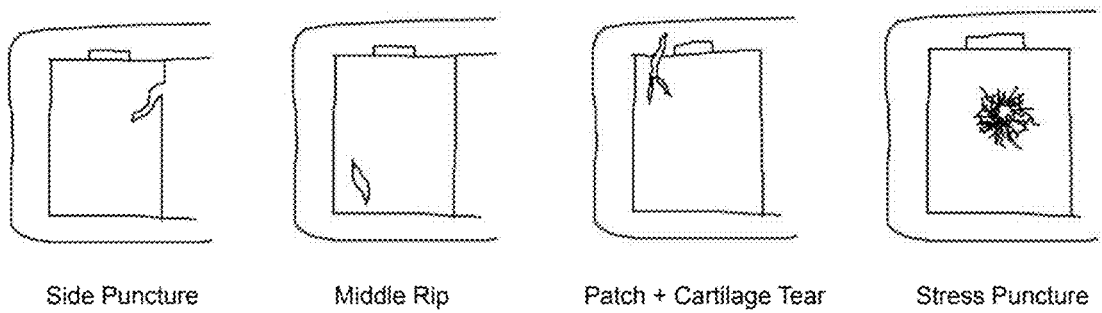
FIG. 8 illustrates different view of Punctured cartridge according to one of the aspects of the present invention.

In an embodiment, FIG. 8 illustrates the different examples of different tears, or punctures that could happen to a cartridge from the side or if there was a middle rip, or if the patch and cartilage tared or if there was like a stress puncture in the middle of this cartridge.

Figure 9:
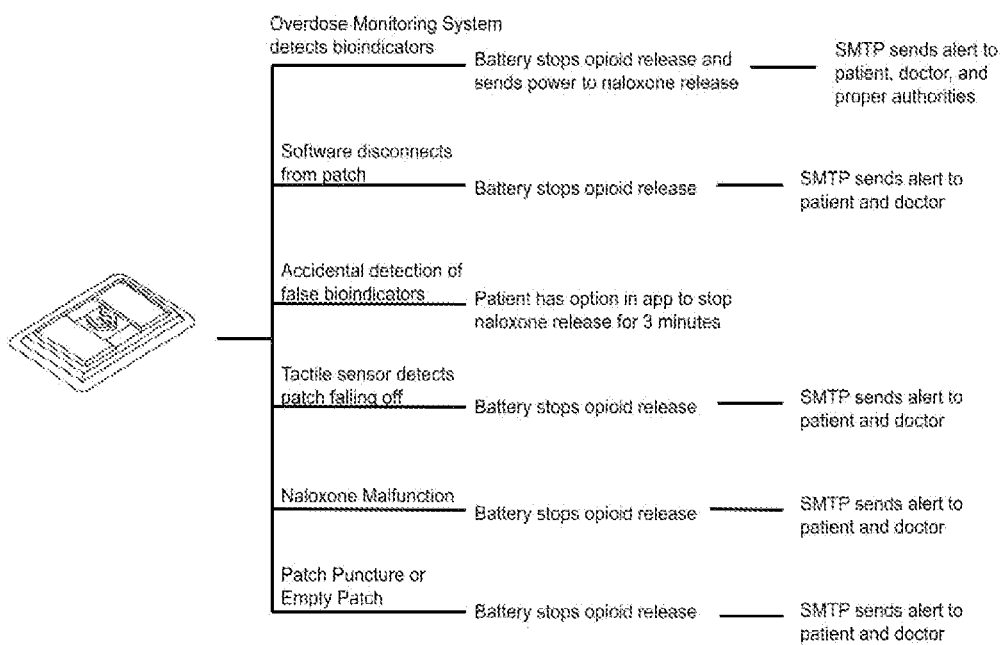
FIG. 9 is a diagram to map out any issues that could go wrong with the with the patch, and to solve those issues.

In an embodiment, FIG. 9 is a diagram to map out any issues that could go wrong with the with the patch, and to solve those issues. Start from the patch, If the overdose monitoring system does detect bio indicators, as in it does detect an overdose, the battery stops opioid release and sends power to the Naloxone release instead and immediately the BLE module is able to connect to the app and tell the app that it needs to send an alert to patient, the doctor as well as proper authorities. Second safeguard is if there is any disconnection in regard to the software as in the microcontroller or the app or module, any type of issue there, the battery immediately stops opioid release and again, an alert is sent to both the patient and the doctor. Since it is not an emergency that it was disconnected, no need to consult with emergency services at that time. If there is an accidental detection of false bio indicators, the patient has an option in the app to stop Naloxone release for three minutes. If they are able to say, Okay, I'm not having an overdose inside of the app, then the app was completely shut off and then further issue or further action can be taken by the patient and the doctor at a later time. The fourth issue is if the tactile sensor detects the patch falling off, the battery stops the opiate opioid release, and the alert is sent to the patient and doctor. This is referred to as locked patch. This is what would happen in that case. If there was a Naloxone malfunction, say for example, Naloxone was unable to be deployed, or any type of issue with the Naloxone drug itself, the battery would stop opioid release and again, an alert would be sent to the patient and doctor. And then as mentioned in FIG. 8 if there was some type of puncture, or if the patch was emptied, which could be noted in the app, the battery stops opioid release, and the SMTP service sends an alert again to the patient and doctor.

Figure 10:
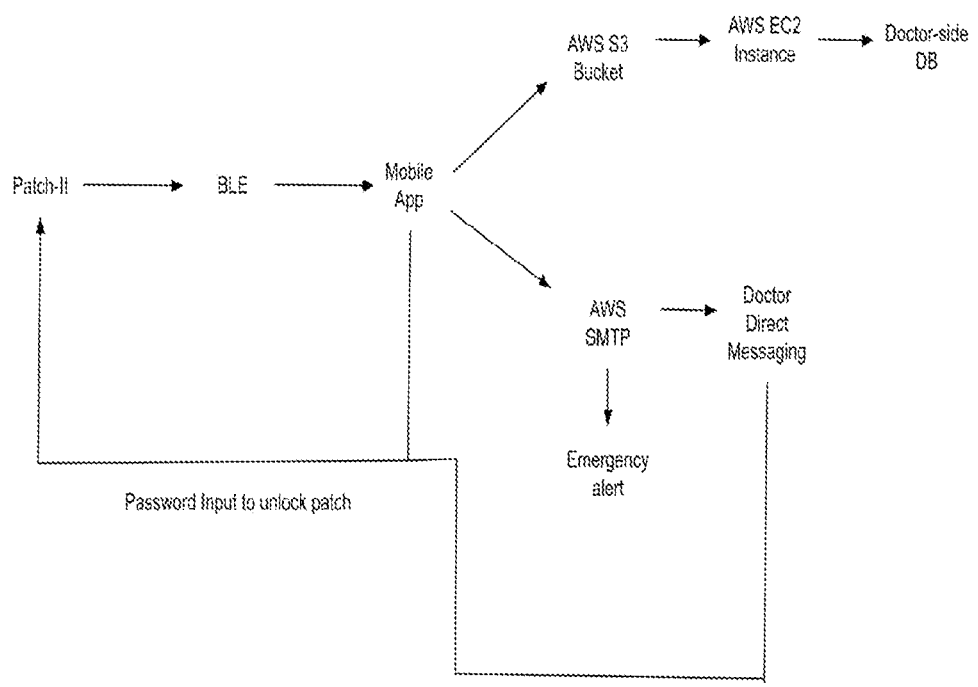
FIG. 10 illustrates schematic diagram of Software flow.

In an embodiment, FIG. 10 illustrates schematic diagram of Software flow which start with patch unit, Bluetooth module is present to deploy and send the data towards mobile app. By using this user can determine any of their vitals like whether the patch is currently operating or not. All the relevant data is first sent to AWS S3 and AWS EC2 instance. Essentially these two things allow for the data to be sent to some cloud, database online. It can track and monitored by doctors as well. The data sent on this cloud database can be shown on some other doctor side application, or they can be the raw data itself within some online server. the actual data that is being transmitted can also go to SMTP. It uses the AWS SMTP role to essentially direct messages or send an emergency alert towards if there are anything wrong with the patch. The actual user can always communicate with the doctor by texting them or it through the app itself. If vitals reaching an alarming level, Naloxone was deployed. In this case, there is a need to alert actual authorities or loved ones. The AWS SMTP, Simple Mail Transfer Protocol tool to be able to do this. On the doctor side, the password input to unlock the patch and let it start deploying is given by the doctor's permission itself through the doctor side, database, and back end. So once that happens, that password input can is the only thing that can trigger the patch to start sending data towards a mobile app. Without that, it won't be able to deliver or won't be able to even work. However, the doctors act as the main safeguard that password safeguard to make sure the patch unit is not being abused or accidentally used in any kind of way.

Figure 11:
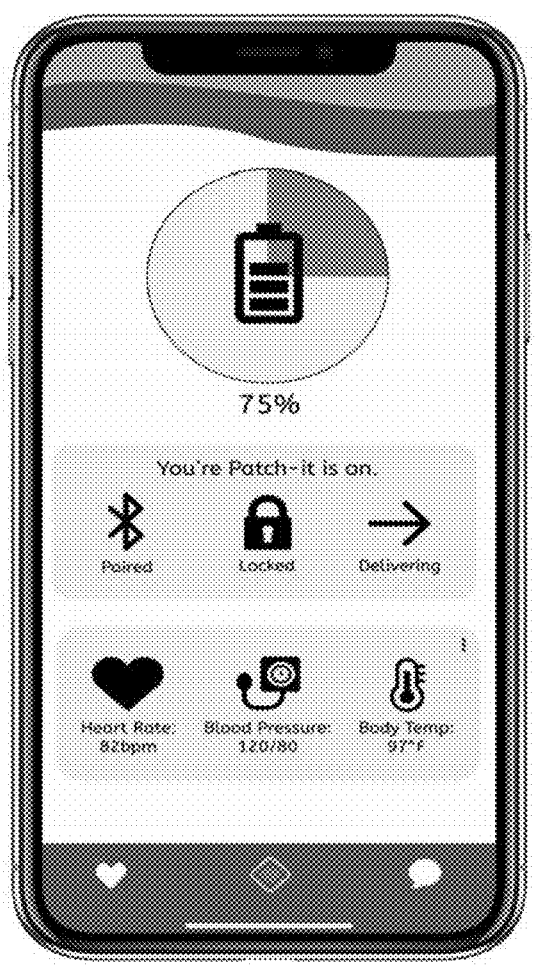
FIG. 11 illustrates a mobile App screen of a user.

In an embodiment, FIG. 11 illustrates mobile App screen which can be access by using password; wherein Battery levels are Boolean values, like whether it's locked right now, whether it's delivering, and all the vitals that the patch is tracking, or all can be tracked through that in the app itself, as well as messaging.

Figure 12:
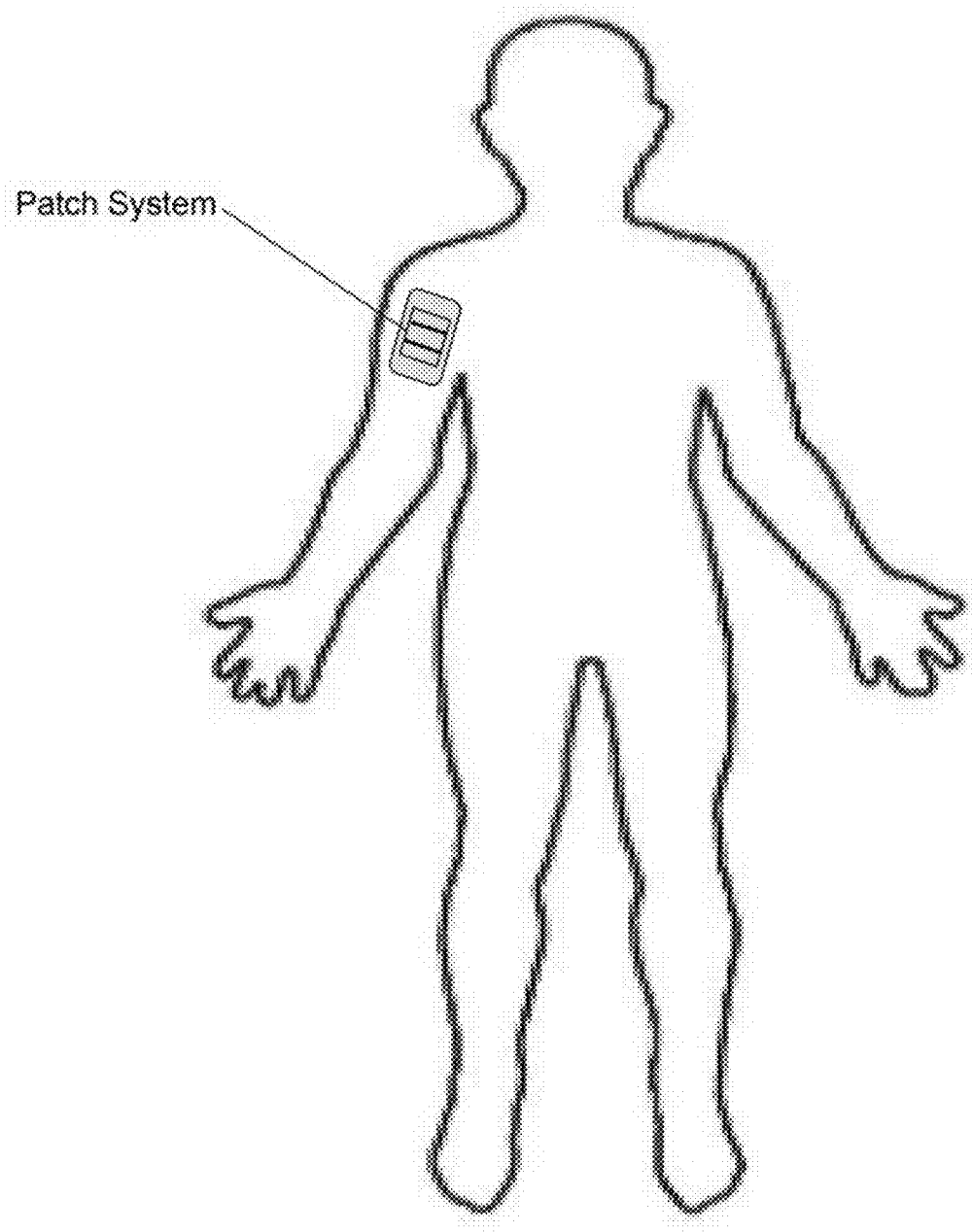
FIG. 12 illustrates a placement of patch system on the skin of a user.

In an embodiment, FIG. 12 showing placement of patch system on the skin of a user. This does not have to be exact as there is no reason that it needs to be in exactly a certain place. But in general, the patch would be placed on the upper arm to allow for easy access as well as allow for, there couldn't be any issue that could go wrong with it in terms of it falling off or anything like that. With it being on the arm, the user would know to be careful.

In an embodiment, Non-addicts could use patch for convenience. Whenever patients go through intense surgeries or procedures, they are given prescribed painkillers or opioids. On average, patients use opioids for three days or less, and more than seven days will rarely be needed. Clinicians evaluate benefits and harms within 1 to 4 weeks of starting opioid therapy for dose escalation. During the time any patients use opioids, Patch will be an autonomous and self-controlled drug delivery system which would save time and effort for patients, ensure that under/overdosing is not a problem, and it would prevent possible addiction (to the opioids, as it would be minimal and scheduled).

In an embodiment, patients who are non-addicts to these opioids still require long-term and short-term prescriptions to these drugs. Addiction and/or human error can always cause issues with the drug, and because these drugs can cause life-threatening issues if misused or mis-administered, it is important for these patients to have a safer option which would also provide them with a more convenient solution.

Patch system has a very comfortable shape and size (design) which would be the best option for patients. They would take these drugs without even feeling the actual process of the drugs being released into the body. This will increase their overall productivity and will help them shift their focus from the pain and painkillers (their mindset will change, and they would be less focused on the medications).

INCORPORATION BY REFERENCE

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

U.S. Pat. No. 8,357,114B2
U.S. Pat. No. 6,745,071B1
US20190231707A1
US20080004564A1
US20070083186A1
U.S. Pat. No. 6,424,862B1
U.S. Ser. No. 10/610,128B2
U.S. Pat. No. 8,911,773B2
US20200289488A1
U.S. Ser. No. 10/806,924B2
U.S. Pat. No. 8,696,637B2
U.S. Pat. No. 9,314,527B2
US20160235975A1
U.S. Ser. No. 10/745,601B2
U.S. Pat. No. 9,944,835B2
U.S. Ser. No. 10/647,032B2
U.S. Pat. No. 7,004,929B2
US20110144586A1
US20180214631A1
U.S. Pat. No. 7,344,894B2
U.S. Ser. No. 10/603,440B2
U.S. Pat. No. 7,717,877B2
U.S. Pat. No. 8,480,632B2

What is claimed is:

1. A transdermal drug delivery system comprising a patch; the patch comprising:
a cartridge comprising a drug;
a bio-sensor and a non bio-sensor;
an active delivery pad comprising an electrode for delivery of the drug into a tissue via iontophoresis;
a power source of electrical energy connected to the electrode;
a microcontroller configured to control a release of the drug;
wherein the patch is attached to the tissue via an adhesive pad, and a top of the patch is covered with a sheet;
wherein the bio-sensor is configured to detect a physiological parameter of a patient wearing the patch;
wherein the non bio-sensor is configured with a software to: a) control working of the patch via an app, b) send an information about a physiological parameter of the patient to a database system, c) alert the patient about a working condition of the patch;
wherein opening and closing of the cartridge are controlled by the app and the cartridge is capable to be refilled with the drug successively;
wherein the microcontroller adapted to analyze a medical characteristic of the patient to determine a symptom that indicates an opioid overdose in the patient;
wherein the patch has a password protection system; and
wherein the patch is a biodegradable patch.

2. The transdermal drug delivery system of claim 1, wherein the bio-sensor comprises a blood pressure sensor, a temperature sensor, and a heart rate sensor, a tactile sensor; and wherein the non bio-sensor comprises a BLE sensor.

3. The transdermal drug delivery system of claim 1, wherein the patch comprises a first cartridge comprising a first drug and a second cartridge comprising a second drug wherein the first cartridge and second cartridge are separated from each other.

4. The transdermal drug delivery system of claim 1, wherein the electrode comprises of zinc and silver chloride electrode, and wherein the drug comprises an opioid drug, non-opioid drug, or an opioid antagonist comprising Naloxone.

5. The transdermal drug delivery system of claim 1, wherein the release of the drug starts on a signal, wherein the signal is regulated manually comprising a release button and/or automatically based on physiological condition of the patient.

6. The transdermal drug delivery system of claim 1, wherein the working condition includes an overdose of the drug, an accidental loss of the patch, a defunct power source, an empty cartridge or any combination thereof.

7. The transdermal drug delivery system of claim 1, wherein the patch further comprises a first system to replace the power source and/or to recharge the power source, and a second system to refill the cartridge.

8. A system comprising a patch; the patch comprising:
a tissue contacting side comprising an adhesive layer and an active delivery pad;
a non-tissue contacting side comprising:
a biosensor to configure a medical characteristic of a user wearing the patch,
at least a first electrode and a second electrode wherein each of the first electrode and the second electrode is coupled respectively to a first reservoir and a second reservoir;
wherein the first reservoir comprising a first cartridge containing a first drug selected from the group consisting of an opioid, an opioid agonist or a partial opioid agonist and the second reservoir comprising a second cartridge containing a second drug consisting of an opioid antagonist,
a source of electric power connected in a circuit,
a microcontroller configured for controlling current flow in said circuit according to a signal from the biosensor to enable plurality of successive doses of said first drug and/or said second drug, and
a non bio-sensor configured with a software to: a) control working of the patch via an app, b) send an information about a physiological parameter of the user to a database system, c) alert the user about a working condition of the patch;
wherein the active delivery pad at the tissue contacting side allow for an iontophoretic transdermal delivery of the drug to the user through the tissue contacting side,
wherein the microcontroller is adapted to analyze a medical characteristic of the user to determine a symptom that indicates an opioid overdose in the user, wherein opening and closing of the first cartridge and the second cartridge are controlled by the app and the first cartridge and the second cartridge are capable to be refilled with a drug successively, and wherein the patch is a biodegradable patch.

9. The system of claim 8, wherein the non bio-sensor comprises a BLE sensor.

10. The system in claim 8, wherein an electrodes comprise zinc or silver chloride, and wherein an cartridge is reusable.

11. The system of claim 8, wherein the first cartridge and second cartridge are separated from each other.

12. The system of claim 8, wherein the patch has a password protection system.

13. A method to regulate release of a drug comprising:
obtaining the transdermal drug delivery system of claim 1; attaching the patch to a substrate; sending a signal to start an electric current flow; transferring of the drug by the transdermal drug delivery system, the transdermal drug delivery system comprising an iontophoretic transdermal delivery system; wherein release of the drug is controlled by the microcontroller.

14. The method of claim 13 wherein release rate of the drug is $$R_d = \frac{t_d I M_d}{z_d F}$$

wherein $R_d$ is a rate of transdermal delivery of the drug;
$t_d$ is a transport number or a fraction of charge that is carried by an ion of the drug;
I is a value of the electric current flow;
$M_d$ is a molecular weight of the ion of the drug;
$z_d$ is a valence of the ion of the drug; and
F is Faraday's constant.

15. A system comprising a patch; the patch comprising:
a substrate having a tissue contacting side and a non-tissue contacting side,
electrodes comprising a first electrode and a second electrode,
a first reservoir comprising a first cartridge comprising a first drug selected from the group consisting of an opioid, an opioid agonist or a partial opioid agonist and a second reservoir comprising a second cartridge comprising a second drug consisting of an opioid antagonist,
a source of electric power connected in a circuit between the first reservoir and the second reservoir,
a microcontroller configured for controlling a current flow in the circuit to enable a plurality of successive doses of the first drug and/or the second drug from the first reservoir and/or the second reservoir; and
a non bio-sensor configured with a software to: a) control working of the patch via an app, b) send an information about the physiological parameter detected of a user by a biosensor to a database system, c) alert the user about a working condition of the patch;
wherein the working condition of the patch is selected from the group consisting of functioning of the biosensor, an overdose of the drug, an accidental loss of the patch, a defunct power source, a real time condition of the first cartridge and the second cartridge, or combinations thereof,
wherein each of the first electrode and the second electrode are coupled to the first reservoir and the second reservoir respectively,
wherein the tissue contacting side comprises an adhesive layer that allows transdermal delivery to a patient of the first drug and the second drug, and
wherein the system is configured to be an automatic and self-controlled transdermal drug delivery system;
wherein the microcontroller is adapted to analyze a medical characteristic of the user to determine a symptom that indicates an opioid overdose in the user,
wherein opening and closing of the first cartridge and the second cartridge are controlled by the app and the first cartridge and the second cartridge are capable to be refilled with a drug successively, and
wherein the patch is a biodegradable patch.

16. The system in claim 15, wherein the first reservoir and/or the second reservoir comprises a cartridge that is configured to hold a plurality of drug forms.

17. The system of claim 15, wherein the first reservoir and the second reservoir are separated from one another.

18. The system of claim 15, wherein the biosensor coupled to the microcontroller verify a medical characteristic of the user prior to delivery of the opioid, the opioid agonist or the partial opioid agonist.

19. The system of claim 18, wherein the biosensor comprises a pulse oximeter, a heart rate sensor, an ECG sensor, a skin sensor, a temperature sensor, and/or a blood flow sensor.

20. The system of claim 15, wherein the microcontroller is further configured to send an alert or notification wirelessly upon detection of the symptom.

* * * * *